US009076565B2

(12) United States Patent
Shiraki et al.

(10) Patent No.: US 9,076,565 B2
(45) Date of Patent: Jul. 7, 2015

(54) IMAGE PROCESSING APPARATUS, IMAGE PROCESSING METHOD, AND PROGRAM

(71) Applicant: Sony Corporation, Tokyo (JP)

(72) Inventors: Hisakazu Shiraki, Kanagawa (JP); Hiromi Yoshinari, Kanagawa (JP); Yoshinori Takagi, Kanagawa (JP); Yuki Sugie, Tokyo (JP)

(73) Assignee: SONY CORPORATION (JP)

( * ) Notice: Subject to any disclaimer, the term of this patent is extended or adjusted under 35 U.S.C. 154(b) by 56 days.

(21) Appl. No.: 14/075,056

(22) Filed: Nov. 8, 2013

(65) Prior Publication Data
US 2014/0140484 A1    May 22, 2014

(30) Foreign Application Priority Data

Nov. 16, 2012 (JP) ................................. 2012-251842
Jul. 12, 2013  (JP) ................................. 2013-146769

(51) Int. Cl.
| G21K 1/04 | (2006.01) |
| A61B 6/00 | (2006.01) |
| A61B 6/06 | (2006.01) |
| H05G 1/70 | (2006.01) |

(52) U.S. Cl.
CPC . *G21K 1/043* (2013.01); *A61B 6/06* (2013.01); *A61B 6/4064* (2013.01); *A61B 6/486* (2013.01); *A61B 6/5235* (2013.01); *A61B 6/54* (2013.01); *H05G 1/70* (2013.01); *H01J 2235/068* (2013.01)

(58) Field of Classification Search
USPC .................................................. 378/98.12, 92
See application file for complete search history.

(56) References Cited

U.S. PATENT DOCUMENTS

2010/0080342 A1* 4/2010 Takahashi ...................... 378/22

FOREIGN PATENT DOCUMENTS

JP    2009-025296    2/2009

* cited by examiner

*Primary Examiner* — Kiet T Nguyen
(74) *Attorney, Agent, or Firm* — Sheridan Ross P.C.

(57) ABSTRACT

There is provided an image processing apparatus including a processing unit configured to superimpose a plurality of X-ray images that are based on X-ray detection data representing detection results obtained by detecting a plurality of times in a time-division manner parallel beam X-rays output from a ray source including a plurality of X-ray sources that output parallel beam X-rays.

15 Claims, 18 Drawing Sheets

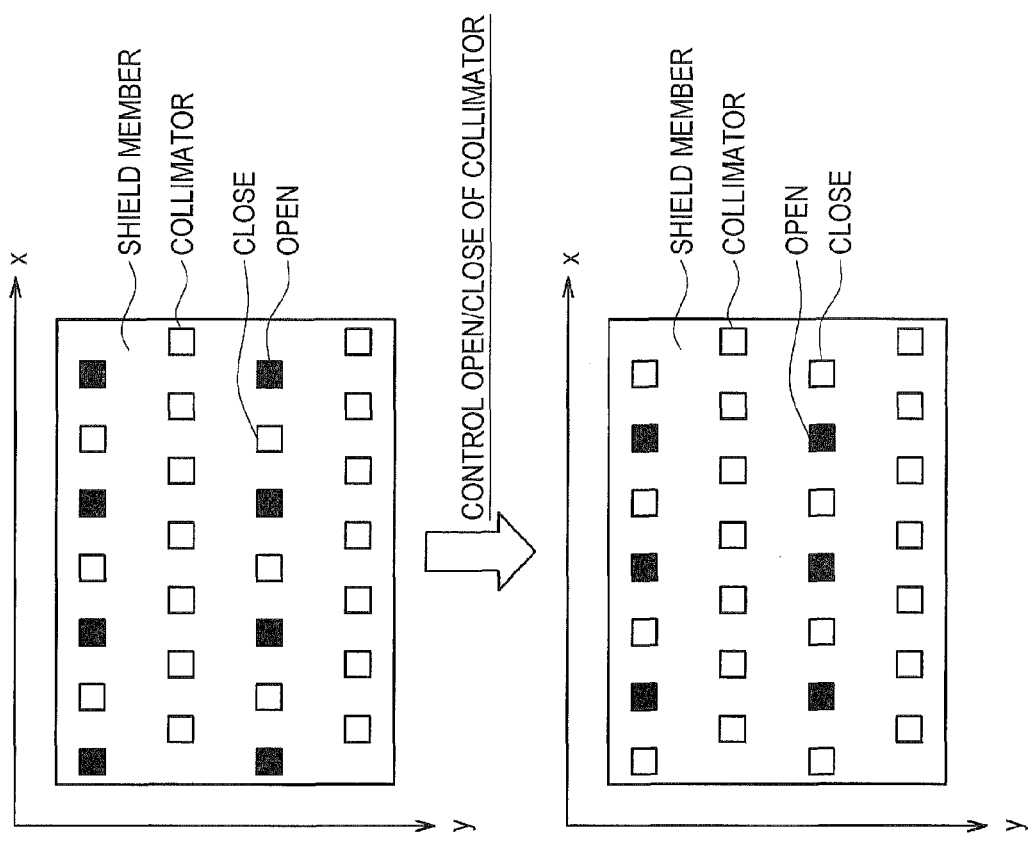
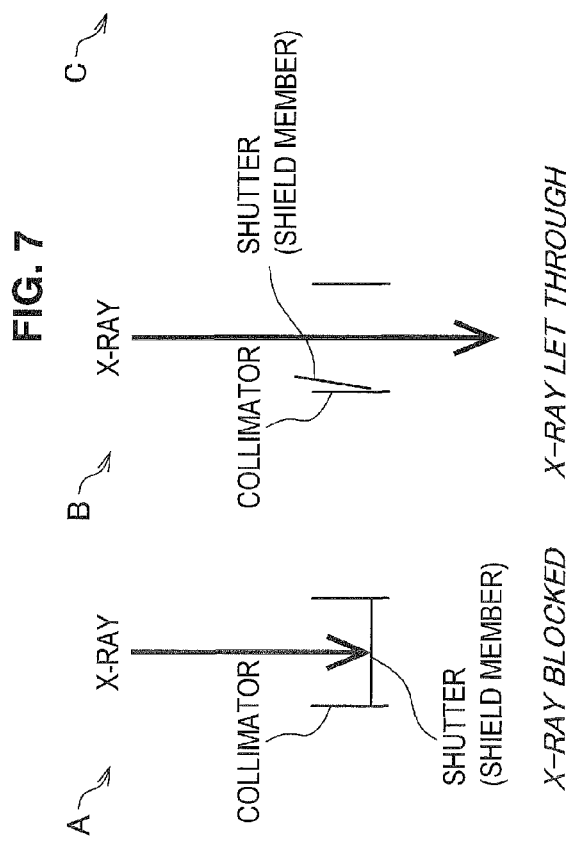
FIG. 7

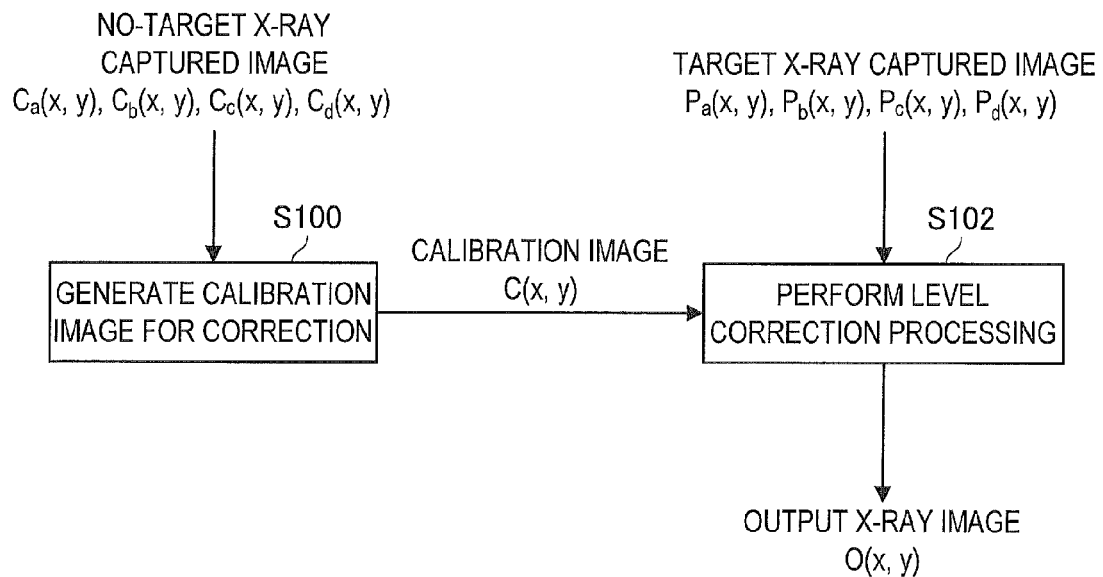
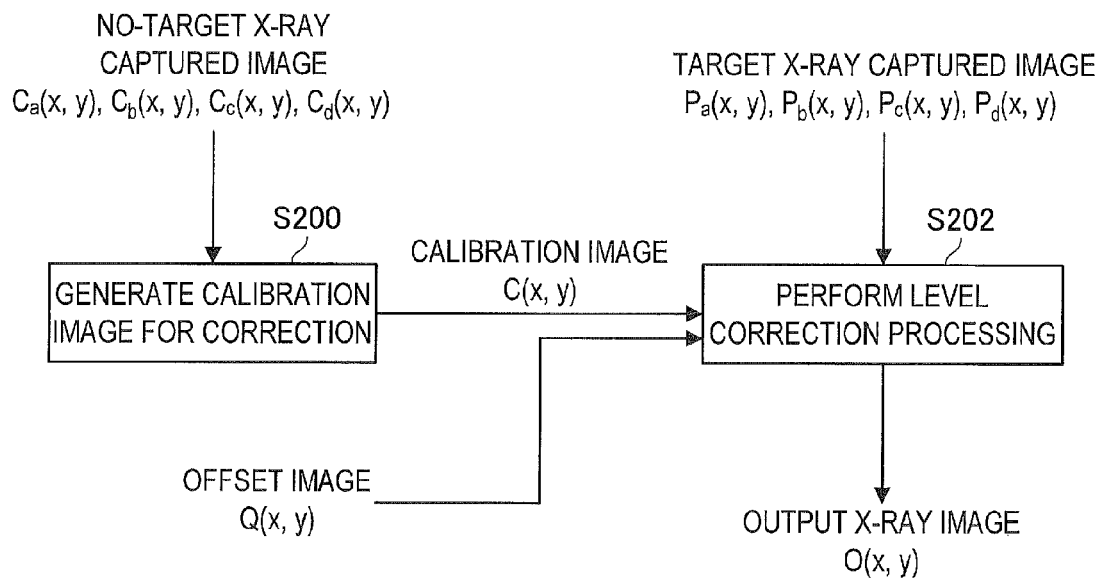

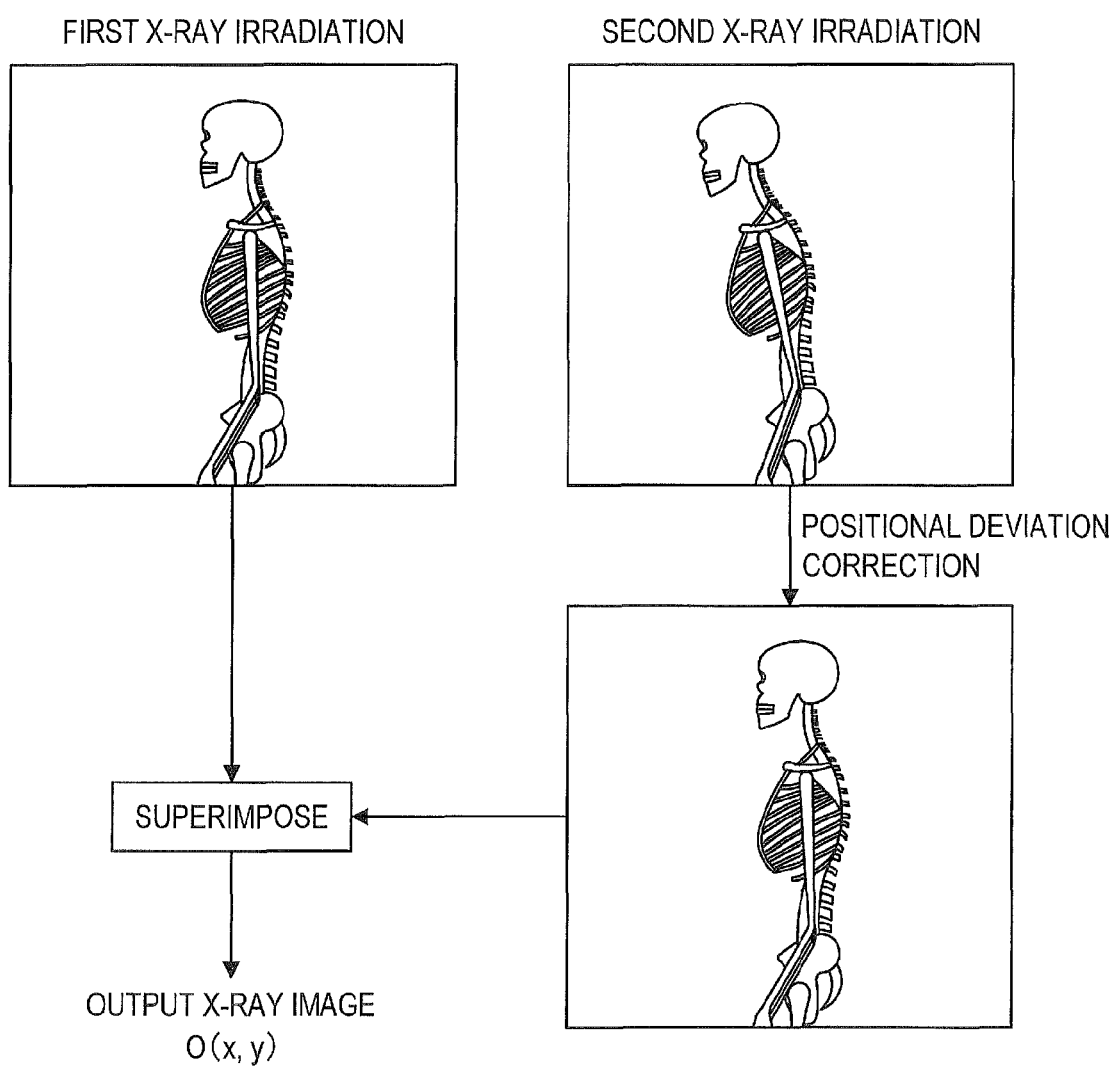

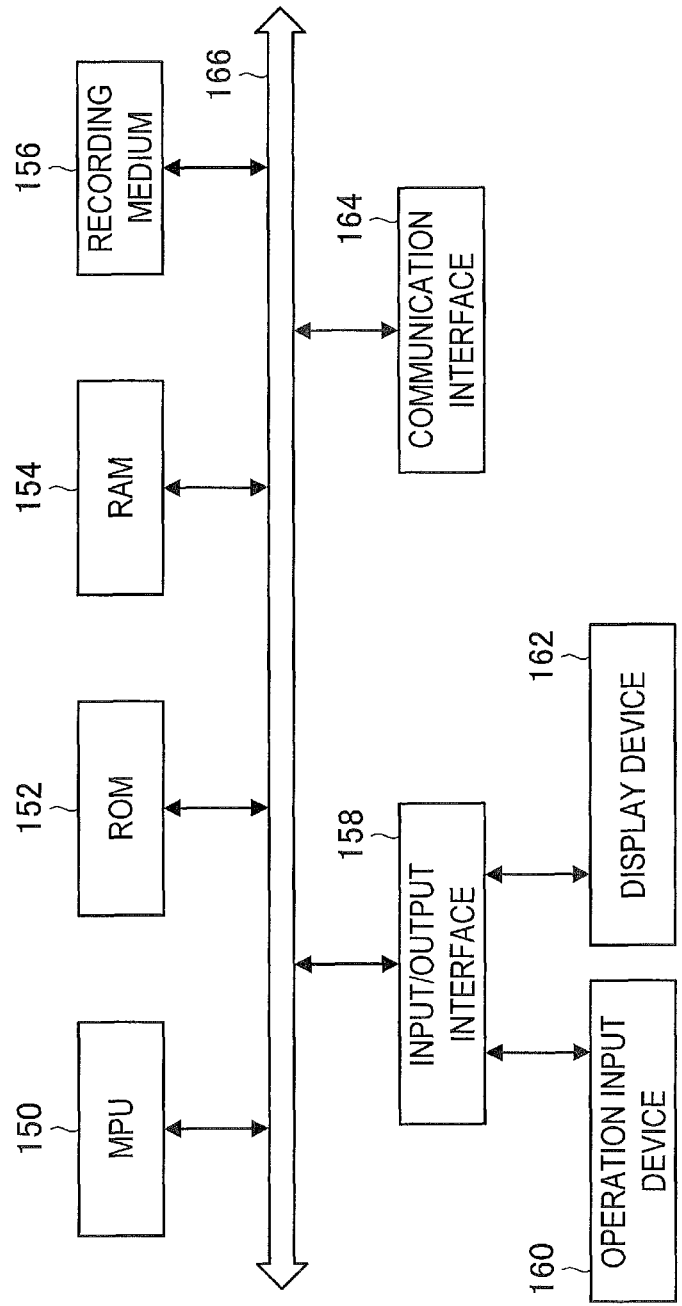

IMAGE PROCESSING APPARATUS, IMAGE PROCESSING METHOD, AND PROGRAM

CROSS REFERENCE TO RELATED APPLICATIONS

This application claims the benefit of Japanese Priority Patent Application JP 2012-251842 filed Nov. 16, 2012, and Japanese Priority Patent Application JP 2013-146769 filed Jul. 12, 2013, the entire contents of each of which are incorporated herein by reference.

BACKGROUND

The present disclosure relates to an image processing apparatus, an image processing method, and a program.

For example, a CT (computed tomography) apparatus (or a CT system; hereinafter, the same) that utilizes X-rays output from an X-ray source or an apparatus (or a system; hereinafter, the same) having a tomosynthesis function that utilizes X-rays is widely used in the medical field, for example.

Further, technology is also being developed that will be based on parallel beam X-rays as the X-rays output from an X-ray source. An example of technology for creating a tomosynthesis image by making parallel X-rays be incident a plurality of times on a target at differing angles is described in JP-A-2009-25296, for example.

SUMMARY

X-rays tend to spread out the further away they are from the X-ray source that outputs the X-rays, for example. Consequently, an unevenness in the intensity of the X-rays can occur in a detection result of X-rays detected by a detector that detects X-rays output from such an X-ray source. Further, if an unevenness in the X-ray intensity does occur, it is not likely that a clear X-ray image will be obtained even if the X-ray detection data representing the detection results of the X-rays is processed.

Here, an example of a countermeasure for suppressing the occurrence of such an unevenness in the X-ray intensity is to, for example, suppress the spreading of the X-rays by outputting parallel beam X-rays by designing a collimator like that illustrated in JP-A-2009-25296. Therefore, like in JP-A-2009-25296, for example, when combining a plurality of projection images each obtained from a different angle by making parallel X-rays be incident a plurality of times on a target at differing angles, there is a chance that a clearer X-ray image might be obtained.

However, even if the spreading of X-rays is suppressed by outputting parallel beam X-rays as described above, for example, the spreading of the X-rays is not eliminated. Consequently, like in JP-A-2009-25296, for example, even if a plurality of projection images each obtained from a different angle by making parallel X-rays be incident a plurality of times on a target at differing angles were combined, a clearer X-ray image might not be obtained due to the unevenness in intensity of the detected X-rays, for example. Therefore, even if the technology described in JP-A-2009-25296, for example, is used, the quality of the X-ray image might not be improved.

According to an embodiment of the present disclosure, there is provided a novel and improved image processing apparatus, image processing method, and program capable of improving the quality of an X-ray image.

According to an embodiment of the present disclosure, there is provided an image processing apparatus including a processing unit configured to superimpose a plurality of X-ray images that are based on X-ray detection data representing detection results obtained by detecting a plurality of times in a time-division manner parallel beam X-rays output from a ray source including a plurality of X-ray sources that output parallel beam X-rays.

According to an embodiment of the present disclosure, there is provided an image processing method including superimposing a plurality of X-ray images that are based on X-ray detection data representing detection results obtained by detecting a plurality of times in a time-division manner parallel beam X-rays output from a ray source including a plurality of X-ray sources that output parallel beam X-rays.

According to an embodiment of the present disclosure, there is provided a program that causes a computer to execute superimposing a plurality of X-ray images that are based on X-ray detection data representing detection results obtained by detecting a plurality of times in a time-division manner parallel beam X-rays output from a ray source including a plurality of X-ray sources that output parallel beam X-rays.

According to one or more of embodiments of the present disclosure, the quality of an X-ray image can be improved.

BRIEF DESCRIPTION OF THE DRAWINGS

FIG. 7 is an explanatory diagram illustrating a second example of ray source control processing according to an embodiment of the present disclosure;

FIG. 11 is an explanatory diagram illustrating an example of processing performed in an image processing method according to an embodiment of the present disclosure;

FIG. 12 is an explanatory diagram illustrating an example of processing performed in an image processing method according to an embodiment of the present disclosure;

FIG. 13 is an explanatory diagram illustrating an example of processing performed in an image processing method according to an embodiment of the present disclosure;

FIG. 21 is an explanatory diagram illustrating an example of a hardware configuration of an image processing apparatus according to an embodiment of the present disclosure.

DETAILED DESCRIPTION OF THE EMBODIMENT(S)

Figure 1:
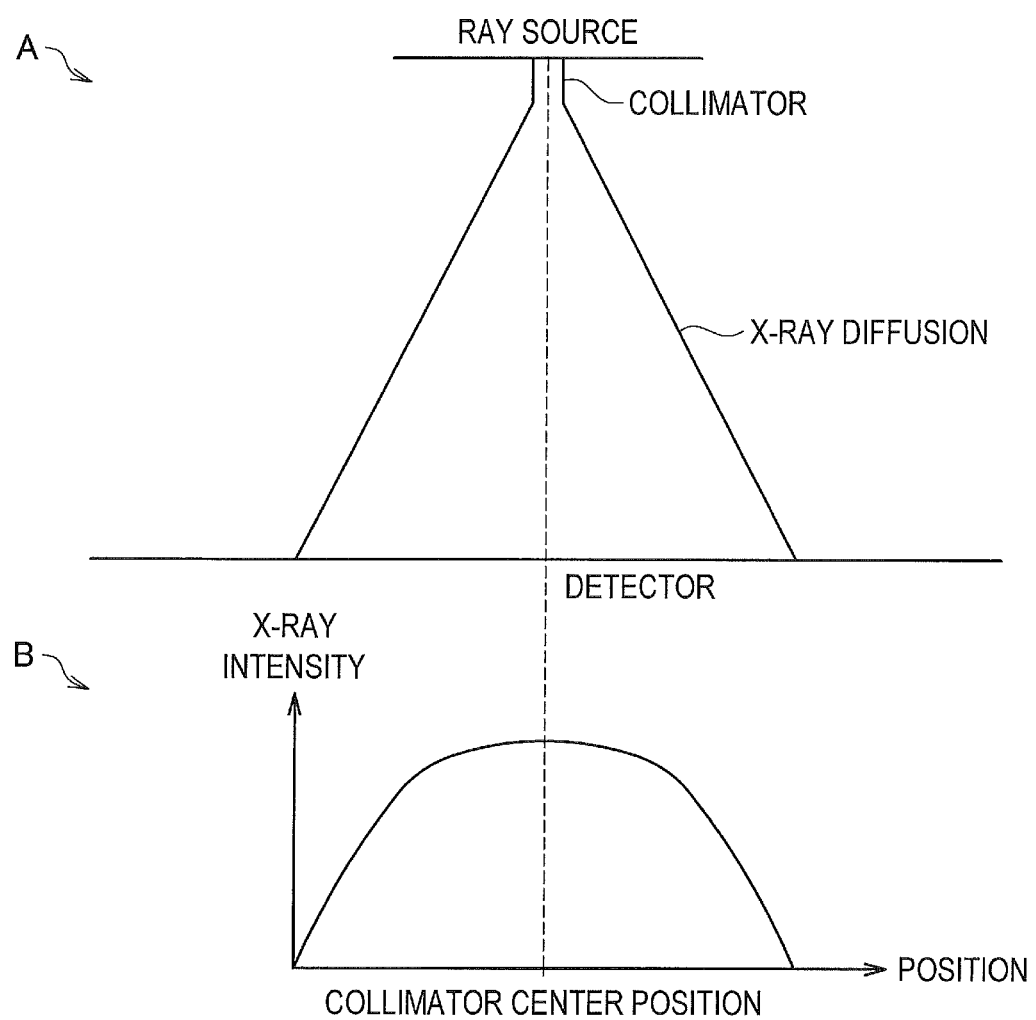
FIG. 1 is an explanatory diagram illustrating an outline of an image processing method according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, the description will be made in the following order.
1. Image processing method according to the present embodiment
2. Image processing apparatus according to the present embodiment
3. Program according to the present embodiment (Image Processing Method According to the Present Embodiment)

Before describing the configuration of the image processing apparatus according to the present embodiment, first, the image processing method according to the present embodiment will be described. In the following, the image processing method according to the present embodiment will be described based on an example in which the image processing apparatus according to the present embodiment performs the processing performed in the image processing method according to the present embodiment.

(1) Outline of the Image Processing Method According to the Present Embodiment

As described above, although it is possible to suppress X-ray spread by outputting parallel beam X-rays with a collimator, for example, even if the X-ray spread is suppressed, the X-ray spread is not eliminated. Consequently, even if parallel beam X-rays are output from the ray source, it may not be possible to obtain a clear X-ray image due to unevenness in the intensity of the detected X-rays, for example. Therefore, the quality of the X-ray image might not be improved.

FIG. 1 is an explanatory diagram illustrating an outline of the image processing method according to the present embodiment, which illustrates an example of diffusion of parallel beam X-rays output via a collimator, and an example of intensity unevenness of the detected X-rays that can occur due to the diffusion of the X-rays. Here, FIG. 1A illustrates an image of the diffusion of the parallel beam X-rays output via a collimator, and FIG. 1B illustrates an example of intensity unevenness of the detected X-rays that can occur due to the diffusion of the X-rays illustrated in FIG. 1A.

As illustrated in FIG. 1A, for example, diffusion of the X-rays occurs even if parallel beam X-rays are output via a collimator by the ray source. Due to this X-ray diffusion, intensity unevenness occurs in the X-rays detected by a detector. Therefore, as illustrated in FIG. 1B, for example, if intensity unevenness of the detected X-rays is present, it might not be possible to obtain a clear X-ray image due to this X-ray intensity unevenness.

Accordingly, rather than simply obtaining an X-ray image from X-ray detection data representing a detection result detected from parallel beam X-rays output from an X-ray source that outputs parallel beam X-rays, the image processing apparatus according to the present embodiment obtains an X-ray image by processing X-ray detection data representing each detection result obtained by detecting a plurality of times in a time-division manner parallel beam X-rays output from the ray source according to the present embodiment that includes a plurality of X-ray sources that output parallel beam X-rays.

Figure 2:
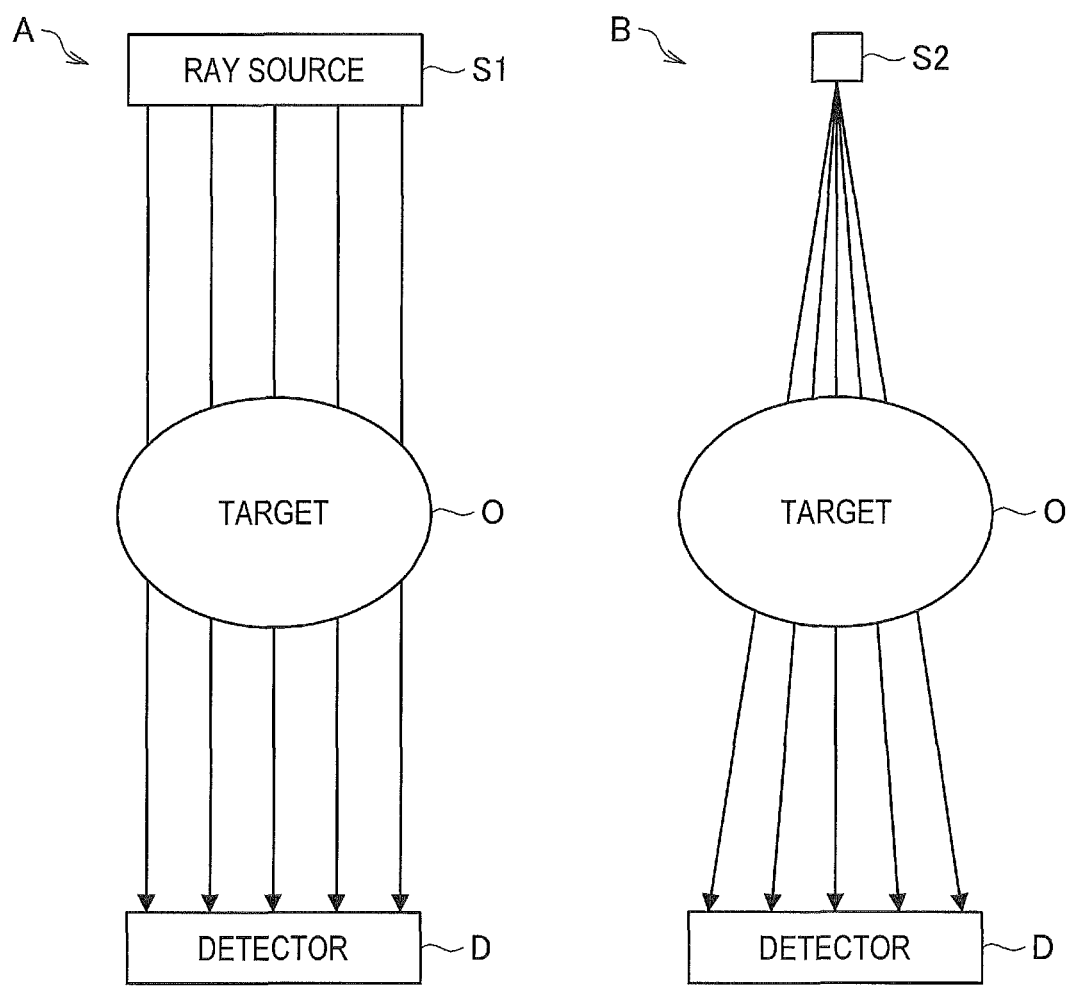
FIG. 2 is an explanatory diagram illustrating a ray source according to an embodiment of the present disclosure.

FIG. 2 is an explanatory diagram illustrating a ray source according to the present embodiment. Here, FIG. 2A is an explanatory diagram illustrating a ray source according to the present embodiment, and FIG. 2B is an explanatory diagram illustrating an example of a known ray source. S1 and S2 in FIG. 2 indicate a ray source from which X-rays are output. Further, O in FIG. 2 indicates a target on which the X-rays are irradiated. D in FIG. 2 indicates a detector for detecting X-rays, such as a FPD (flat panel detector, for example.

The known ray source S2 illustrated in FIG. 2B is, for example, a point ray source, from which X-rays are radially output toward the target O. Further, the radially output X-rays are detected by the detector D, and X-ray detection data representing the detection result is converted into an image.

In contrast, the ray source S1 according to the present embodiment illustrated in FIG. 2A is, for example, a planar ray source in which a plurality of X-ray sources are arranged in a two-dimensional plane, or is a spatial ray source in which a plurality of X-ray sources are arranged in three dimensions. Further, the X-ray sources included in the ray source S1 according to the present embodiment each output parallel beam X-rays. Here, the ray source S1 according to the present embodiment outputs parallel beam X-rays in a time-division manner from the included plurality of X-ray sources by including a collimator, for example.

It is noted that the output of parallel beam X-rays in a time-division manner by the ray source S1 according to the present embodiment is controlled by, for example, a ray source control unit (described below) included in the image processing apparatus according to the present embodiment, or by an external apparatus having a similar function to the ray source control unit (described below). By controlling the output of parallel beam X-rays in a time-division manner by the ray source S1 according to the present embodiment, the image processing apparatus according to the present embodiment can, for example, process a plurality of X-ray images that are based on X-ray detection data representing each detection result obtained by detecting a plurality of times in a time-division manner with a detector, such as the detector included in a below-described detection apparatus according to the present embodiment. The processing performed in the method for controlling the output of parallel beam X-rays in a time-division manner at the ray source according to the present embodiment, i.e., the processing for controlling the acquisition of a plurality of X-ray images that are based on X-ray detection data representing each detection result obtained by detecting a plurality of times in a time-division manner, will be described below.

The image processing apparatus according to the present embodiment processes X-ray detection data representing each detection result obtained by detecting a plurality of times in a time-division manner with a detector, such as the detector included in a below-described detection apparatus according to the present embodiment, detecting the X-rays output from the ray source according to the present embodiment that includes a plurality of X-ray sources like that illustrated by the ray source S1 in FIG. 2A.

More specifically, the image processing apparatus according to the present embodiment obtains an X-ray image corresponding to the target by, for example, superimposing a plurality of X-ray images that are based on X-ray detection data representing each detection result obtained by detecting a plurality of times in a time-division manner (composite processing).

Here, the X-ray detection data according to the present embodiment is, for example, data representing a detection intensity of parallel beam X-rays that have passed through the target that were detected by a detector, such as the detector that is included in the below-described detection apparatus according to the present embodiment. Further, the image processing apparatus according to the present embodiment forms the X-ray images that are based on the X-ray detection data by converting the X-ray detection data into projection data based on Radon conversion, and reconstituting three-dimensional data from the projection data.

Figure 3:
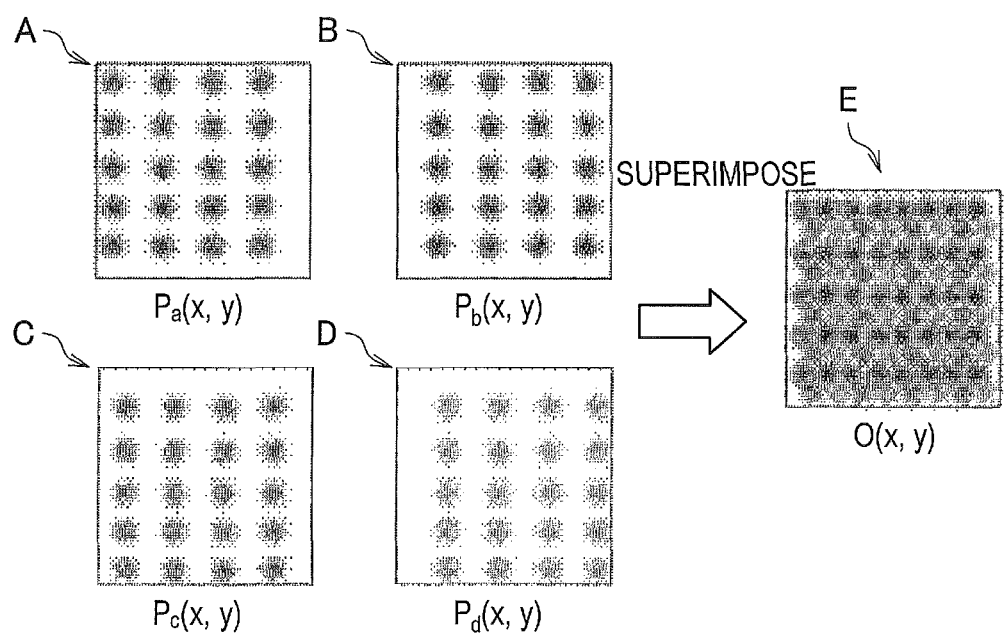
FIG. 3 is an explanatory diagram illustrating an example of processing performed in an image processing method according to an embodiment of the present disclosure.

FIG. 3 is an explanatory diagram illustrating an example of processing performed in the image processing method according to the present embodiment, which illustrates an example of composite processing according to the present embodiment. Here, FIGS. 3A to 3D illustrate examples of a plurality of X-ray images that are based on X-ray detection data representing each detection result obtained by detecting a plurality of times in a time-division manner. Further, FIG. 3E illustrates an example of an X-ray image corresponding to the target obtained by performing the composite processing according to the present embodiment.

It is noted that although FIG. 3 illustrates examples in which the image processing apparatus according to the present embodiment obtains an X-ray image corresponding to the target by superimposing the four X-ray images illustrated in FIGS. 3A to 3D, the number of X-ray images that are superimposed by the image processing apparatus according to the present embodiment is not limited to four. The image processing apparatus according to the present embodiment can, for example, obtain an X-ray image corresponding to the target by superimposing two or more X-ray images that are based on X-ray detection data representing each detection result detected in a time-division manner. More specifically, the image processing apparatus according to the present embodiment can obtain an X-ray image corresponding to the target by, for example, superimposing a plurality of X-ray images that are based on X-ray detection data representing each detection result detected in a time-division manner under various conditions, such as the number of times imaging is performed with X-rays, the imaging order with the X-rays, the position from which the X-rays are output by the ray source according to the present embodiment and the like.

For example, as illustrated in FIG. 3E, the image processing apparatus according to the present embodiment superimposes a plurality of X-ray images like those illustrated in FIGS. 3A to 3D, in which an area overlapping with another X-ray image is not present, that are based on X-ray detection data representing each detection result obtained by detecting a plurality of times in a time-division manner. For example, as illustrated in FIG. 3E, by superimposing a plurality of X-ray images in which an area overlapping with another X-ray image is not present that are based on X-ray detection data representing each detection result obtained by detecting a plurality of times in a time-division manner, an X-ray image corresponding to the target can be obtained.

Figure 4:
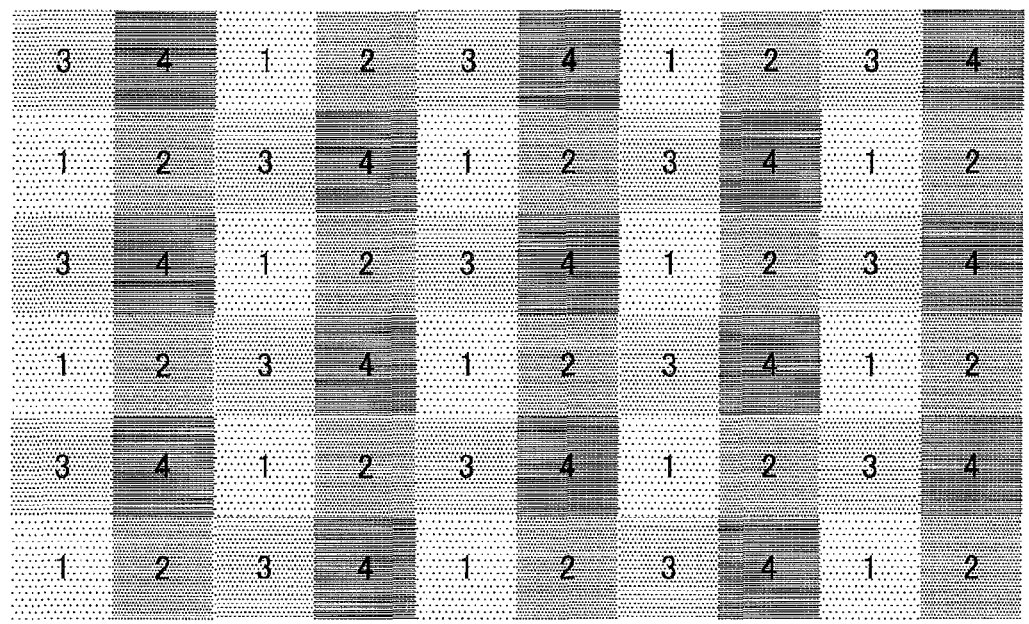
FIG. 4 is an explanatory diagram illustrating a first example of processing performed in an image processing method according to an embodiment of the present disclosure.

FIG. 4 is an explanatory diagram illustrating an example of the processing performed in the image processing method according to the present embodiment. FIG. 4 illustrates an example of a plurality of X-ray images that are based on X-ray detection data that the image processing apparatus according to the present embodiment uses in the composite processing according to the present embodiment. Here, the "1" to "4" in FIG. 4 denote the detection order as detected in a time-division manner. Namely, the example illustrated in FIG. 4 illustrates a case in which an X-ray image corresponding to the target is obtained by the image processing apparatus according to the present embodiment superimposing four X-ray images (from the X-ray image corresponding to the first detection result (the X-ray image corresponding to "1" in FIG. 4) to the X-ray image corresponding to the fourth detection result (the X-ray image corresponding to "4" in FIG. 4) in the same manner as the example illustrated in FIG. 3.

For example, as illustrated in FIG. 4, there is no area overlapping with another X-ray image present in the X-ray images respectively corresponding to "1" to "4". Therefore, the image processing apparatus according to the present embodiment can obtain an X-ray image corresponding to the target by superimposing the X-ray images respectively corresponding to "1" to "4" in FIG. 4.

It is noted that the plurality of X-ray images that are based on X-ray detection data used by the image processing apparatus according to the present embodiment in the composite processing according to the present embodiment are not limited to X-ray images like those in FIG. 4, in which an area overlapping with another X-ray image is not present, that are based on X-ray detection data representing each detection result obtained by detecting a plurality of times in a time-division manner.

For example, the plurality of X-ray images according to the present embodiment that are based on X-ray detection data representing each detection result obtained by detecting a plurality of times in a time-division manner may include, in addition to a plurality of X-ray images like those in FIG. 4 in which an area overlapping with other X-ray images is not present, an X-ray image in which an area overlapping with each of the plurality of X-ray images in which an overlapping with area is not present is present. In the following, for the sake of convenience, X-ray images like those in FIGS. 3 and 4, in which an area overlapping with other X-ray images is not present, that are based on X-ray detection data representing each detection result obtained by detecting a plurality of times in a time-division manner will be referred to as "first X-ray images". Further, in the following, for the sake of convenience, an X-ray image that is based on X-ray detection data representing one detection result among a plurality of detection results obtained by detecting a plurality of times in a time-division manner in which an area overlapping with each of the plurality of the first X-ray images is present will be referred to as a "second X-ray image".

When a plurality of first X-ray images and the second X-ray image are included in the plurality of X-ray images according to the present embodiment that are based on X-ray detection data representing each detection result obtained by detecting a plurality of times in a time-division manner, the image processing apparatus according to the present embodiment corrects each of the plurality of first X-ray images based on the second X-ray image. Further, the image processing apparatus according to the present embodiment superimposes the plurality of corrected first X-ray images.

Figure 5:
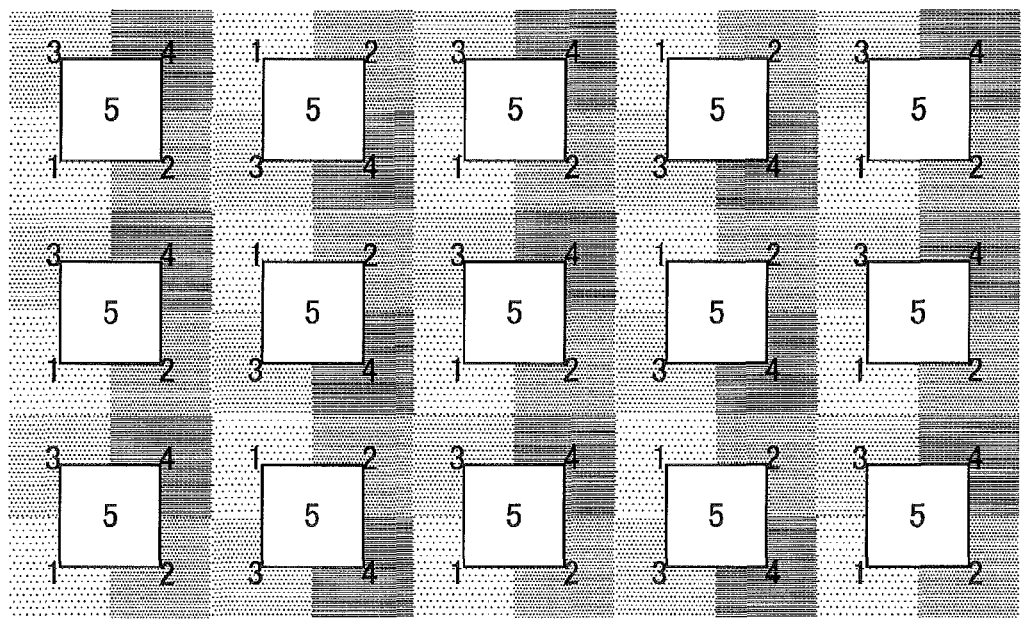
FIG. 5 is an explanatory diagram illustrating a first example of processing performed in an image processing method according to an embodiment of the present disclosure.

FIG. 5 is an explanatory diagram illustrating an example of the processing performed in the image processing method according to the present embodiment. FIG. 5 illustrates another example of a plurality of X-ray images that are based on X-ray detection data that the image processing apparatus according to the present embodiment uses in the composite processing according to the present embodiment. Here, the "1" to "5" in FIG. 5 denote the detection order as detected in a time-division manner. Namely, in the example illustrated in FIG. 5, the X-ray image corresponding to the first detection result (the X-ray image corresponding to "1" in FIG. 5) to the X-ray image corresponding to the fourth detection result (the X-ray image corresponding to "4" in FIG. 5) are first X-ray images. Further, in the example illustrated in FIG. 5, the X-ray image corresponding to the fifth detection result (the X-ray image corresponding to "5" in FIG. 5) is the second X-ray image.

It is noted that although an example is illustrated in FIG. 5 in which the sizes of the X-ray image corresponding to the first detection result (the X-ray image corresponding to "1" in FIG. 5) to the X-ray image corresponding to the fourth detection result (the X-ray image corresponding to "4" in FIG. 5) and the size of the X-ray image corresponding to the fifth detection result (the X-ray image corresponding to "5" in FIG. 5) are the same, the plurality of X-ray images that are based on X-ray detection data that the image processing apparatus according to the present embodiment uses in the composite processing according to the present embodiment are not limited to this. For example, the sizes of the X-ray image corresponding to the first detection result (the X-ray image corresponding to "1" in FIG. 5) to the X-ray image corresponding to the fourth detection result (the X-ray image corresponding to "4" in FIG. 5) and the size of the X-ray image corresponding to the fifth detection result (the X-ray image corresponding to "5" in FIG. 5) may be different. Further, for example, the shapes of the X-ray image corresponding to the first detection result (the X-ray image corresponding to "1" in FIG. 5) to the X-ray image corresponding to the fourth detection result (the X-ray image corresponding to "4" in FIG. 5) and the shape of the X-ray image corresponding to the fifth detection result (the X-ray image corresponding to "5" in FIG. 5) may also be the same or different.

Here, each of the first X-ray images is an X-ray image corresponding to each detection result detected in a time-division manner from parallel beam X-rays output from the ray source according to the present embodiment. Consequently, among the parallel beam X-rays output in a time-division manner from the ray source according to the present embodiment, asymmetry (or an asymmetrical system) can exist in the unevenness of the X-ray intensity due to, for example, differences in the level of degradation of each of the plurality of X-ray sources included in the ray source according to the present embodiment, and differences in the effect of heat by the output of X-rays and the like.

Further, as described above, if asymmetry does exist among the parallel beam X-rays output in a time-division manner from the ray source according to the present embodiment, the X-ray image corresponding to the target that is obtained by the composite processing according to the present embodiment can become an X-ray image in which there is bias due to this asymmetry. Here, an example of an X-ray image in which there is bias due to the above-described asymmetry is the X-ray image illustrated in FIG. 5 in which there is bias in the horizontal direction.

Further, when trying to correct such asymmetry among the parallel beam X-rays output in a time-division manner from the ray source according to the present embodiment, the relationship among each of the first X-ray images is equal. Therefore, when trying to correct such asymmetry among the parallel beam X-rays output in a time-division manner from the ray source according to the present embodiment, it is unclear which first X-ray image (i.e., which detection result that first X-ray image is based on) the correction should be based on to prevent an X-ray image in which there is bias due to the above-described asymmetry.

Accordingly, the image processing apparatus according to the present embodiment corrects each of the plurality of first X-ray images based on a second X-ray image (e.g., the X-ray image corresponding to "5" in FIG. 5". Here, examples of the correction of each of the plurality of first X-ray images based on a second X-ray image include correction of the X-ray intensity (level correction) of the first X-ray images.

Since the second X-ray image according to the present embodiment is an X-ray image in which an area overlapping with each of the plurality of X-ray images is present, by correcting each of the plurality of first X-ray images based on the second X-ray image, the "X-ray image corresponding to the target obtained by the composite processing according to the present embodiment" can be prevented from "becoming an X-ray image in which there is bias due to asymmetry such as that described above". Therefore, the image processing apparatus according to the present embodiment can improve the image quality of an X-ray image even further by correcting each of the plurality of first X-ray images based on a second X-ray image, for example.

In the following, an example will mainly be described in which the image processing apparatus according to the present embodiment obtains an X-ray image corresponding to the target by, as illustrated in FIGS. 3 and 4, superimposing four X-ray images in which an area overlapping with another X-ray image is not present. It is noted that, as described with reference to FIG. 5, the four X-ray images (first X-ray images) that are superimposed by the image processing apparatus according to the present embodiment may also be X-ray images corrected based on a second X-ray image.

As illustrated in FIG. 3, the image processing apparatus according to the present embodiment obtains an X-ray image corresponding to the target by performing (I) composite processing, for example.

Here, as illustrated in FIG. 3, for example, by superimposing a plurality of X-ray images that are based on X-ray detection data representing each detection result obtained by detecting a plurality of times in a time-division manner, the interinfluence among the X-rays output from the X-ray sources included in the ray source according to the present embodiment, such as X-ray sources adjacently arranged in the ray source according to the present embodiment, can be reduced. Further, as illustrated in FIG. 3, by superimposing a plurality of X-ray images that are based on X-ray detection data representing each detection result obtained by detecting a plurality of times in a time-division manner, the influence of intensity unevenness in the detected X-rays, like that illustrated in FIG. 1 for example, which can occur due to X-ray diffusion, can be reduced.

Therefore, the image processing apparatus according to the present embodiment can improve the image quality of an X-ray image by performing the processing (composite processing) of (I) as the processing performed in the image processing method according to the present embodiment.

Further, when a point ray source is used as the ray source, like the known ray source illustrated in FIG. 2B, for example, X-rays of a certain intensity are irradiated on the target in order to obtain an X-ray image corresponding to the target by radially outputting X-rays toward the target.

In contrast, since the image processing apparatus according to the present embodiment can obtain an X-ray image based on the processing (composite processing) of (I), even if the plurality of X-ray sources included in the ray source according to the present embodiment output X-rays that are weaker than the known ray source, the image processing apparatus according to the present embodiment can obtain an X-ray image corresponding to the target. Therefore, when the image processing apparatus according to the present embodiment performs the processing (composite processing) of (I) as the processing performed in the image processing method according to the present embodiment, the target can be subjected to less exposure than when a known ray source is used.

In addition, when a point ray source, like the known ray source illustrated in FIG. 2B, for example, is used in the manner described above as the ray source, X-rays are radially output toward the target. Here, if X-rays are radially output in a manner like a known ray source (when cone beam X-rays or fan beam X-rays are output), mixing of the data from a plurality of layers of the target on which the X-rays hit occurs in the projection data due to the spread in the detection intensity at the detector and unevenness in the detection results. Further, in order to strictly carry out the reconstitution of three-dimensional data from projection data in which data from various layers is mixed like this, calculations are performed that repeatedly use all of the projection data and all of the reconstitution data. Therefore, when forming an X-ray image having greater accuracy by processing projection data in which X-ray detection data corresponding to the X-rays output from a known ray source has been converted, the calculation costs for forming the X-ray image become very large.

In contrast, for example, in the processing (composite processing) of (I), the image processing apparatus according to the present embodiment forms an X-ray image from each of a plurality of X-ray detection data, which represent each detection result obtained by detecting a plurality of times in a time-division manner, and correspond to the parallel beam X-rays output from the ray source according to the present embodiment like that illustrated in FIG. 2A. Further, the image processing apparatus according to the present embodiment obtains an X-ray image corresponding to the target by superimposing the plurality of X-ray images in the processing (composite processing) of (I). Namely, the image processing apparatus according to the present embodiment does not have to calculate by repeatedly using all of the projection data and all of the reconstituted data on each other like when processing X-ray detection data corresponding to the X-rays output from the known ray source. Therefore, when the image processing apparatus according to the present embodiment performs the processing (composite processing) of (I) as the processing performed in the image processing method according to the present embodiment, the processing can be carried out faster than when the known ray source is used, and the memory amount used in the processing can be decreased.

It is noted that the processing performed in the image processing method according to the present embodiment is not limited to the processing (composite processing) of (I). For example, the image processing apparatus according to the present embodiment may also control the acquisition of the plurality of X-ray images that are based on X-ray detection data representing each detection result obtained by detecting a plurality of times in a time-division manner as the processing performed in the image processing method according to the present embodiment (ray source control processing).

(A) First Example of the Ray Source Control Processing According to the Present Embodiment The image processing apparatus according to the present embodiment controls, for example, the selective output of the parallel beam X-rays from each of the plurality of X-ray sources included in the ray source according to the present embodiment. More specifically, the image processing apparatus according to the present embodiment controls, for example, the ON (state in which X-rays are output)/OFF (state in which X-rays are not output) of each of the plurality of X-ray sources included in the ray source according to the present embodiment.

Figure 6:
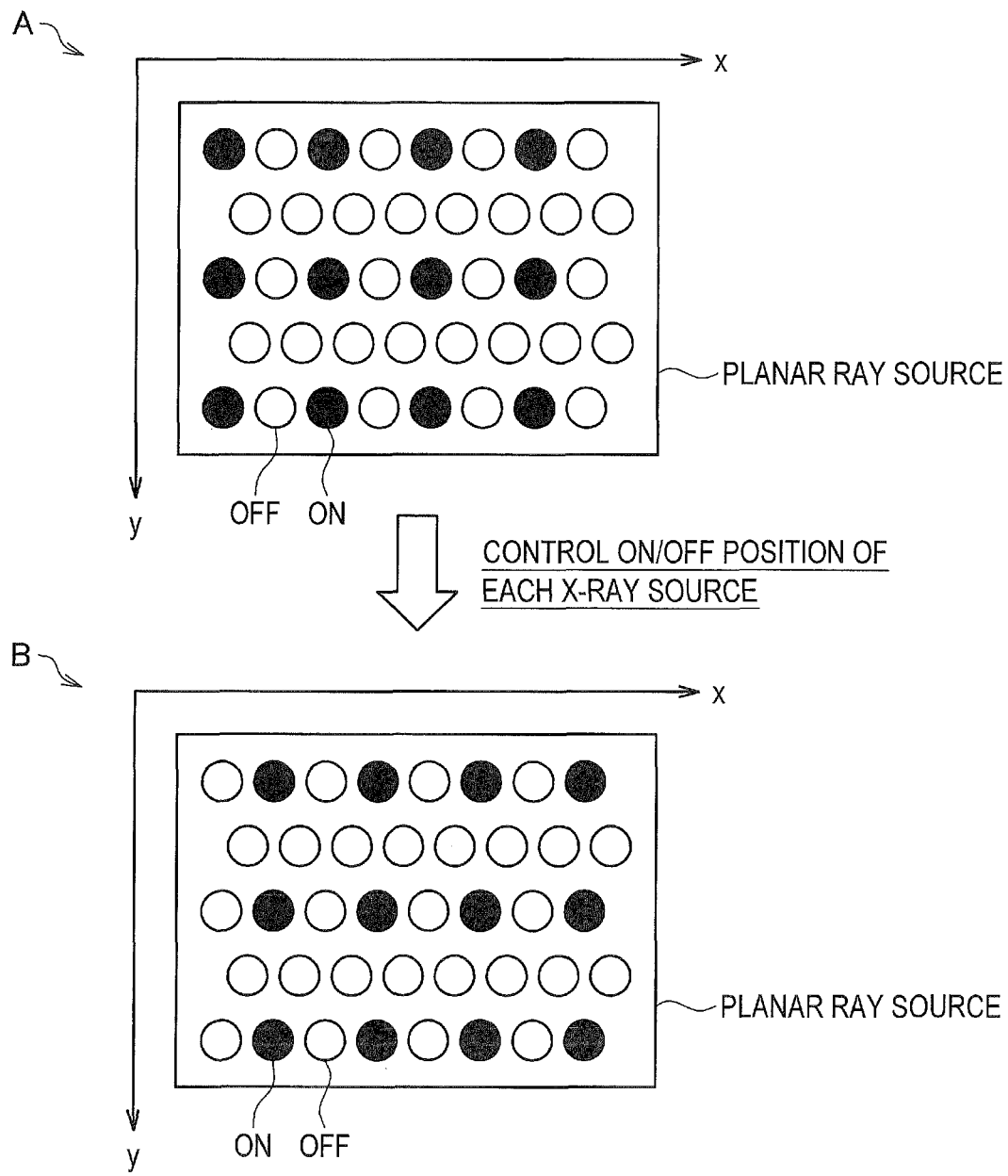
FIG. 6 is an explanatory diagram illustrating a first example of ray source control processing according to an embodiment of the present disclosure.

FIG. 6 is an explanatory diagram illustrating a first example of the ray source control processing according to the present embodiment. Here, in FIG. 6, the ray source according to the present embodiment is illustrated as an example of a planar ray source. Further, FIG. 6A illustrates an example of a state of the ray source according to the present embodiment at a first time point, and FIG. 6B illustrates an example of a state of the ray source according to the present embodiment at a second time point (a time point after the first time point).

For example, as illustrated in FIGS. 6A and 6B, the image processing apparatus according to the present embodiment controls the detection of X-rays in a time-division manner by a detector, such as the detector included in the below-described detection apparatus according to the present embodiment, by controlling the ON/OFF of the output of the X-rays from each of the plurality of X-ray sources included in the ray source according to the present embodiment. Therefore, the image processing apparatus according to the present embodiment can acquire from the detector a plurality of X-ray images that are based on X-ray detection data representing each detection result obtained by detecting a plurality of times in a time-division manner, and perform the processing (composite processing) of (I) on the plurality of acquired X-ray images.

(B) Second Example of the Ray Source Control Processing According to the Present Embodiment If the ray source includes a plurality of collimators that selectively let the X-rays corresponding to each of the plurality of X-ray sources through, the image processing apparatus according to the present embodiment controls, for example, the transmission of the X-rays at each collimator.

FIG. 7 is an explanatory diagram illustrating a second example of the ray source control processing according to the present embodiment. Here, FIG. 7A and FIG. 7B illustrate examples of the configuration relating to selective X-ray transmission at the collimator according to the present embodiment. Further, FIG. 7C illustrates an example of a state of the collimator according to the present embodiment at a first time point, and FIG. 7D illustrates an example of a state of the collimator according to the present embodiment at a second time point (a time point after the first time point).

For example, as illustrated in FIGS. 7A and 7B, the collimator according to the present embodiment includes a shutter (shield member) capable of selectively blocking X-rays by opening and closing. Here, examples of the shutter include a metal plate including a metal such as lead or iron capable of blocking X-rays, glass including such a metal and the like. It is noted that the shutter may be formed from an arbitrary substance, as long as it can block X-rays.

The image processing apparatus according to the present embodiment switches between a state in which the shutter is open and a state in which the shutter is closed by, for example, controlling the current to control a magnetic field. It is noted that the shutter opening and closing configuration according to the present embodiment is not limited to the examples illustrated in FIGS. 7A and 7B. The shutter opening and closing configuration according to the present embodiment may be, for example, a mechanism similar to the shutter in the imaging apparatus or some other arbitrary configuration, as long as it can switch between a state in which the shutter is open (state in which X-rays are allowed to pass through) and a state in which the shutter is closed (state in which X-rays are blocked).

For example, as illustrated in FIGS. 7C and 7D, the image processing apparatus according to the present embodiment controls the detection of X-rays in a time-division manner by a detector, such as the detector included in the below-described detection apparatus according to the present embodiment, by controlling the opening/closing (i.e., selective X-ray transmission) of each collimator corresponding to each of the plurality of X-ray sources included in the ray source according to the present embodiment. Therefore, the image processing apparatus according to the present embodiment can acquire from the above-described detector a plurality of X-ray images that are based on X-ray detection data representing each detection result obtained by detecting a plurality of times in a time-division manner, and perform the processing (composite processing) of (I) on the plurality of acquired X-ray images.

(C) Third Example of the Ray Source Control Processing According to the Present Embodiment If the ray source according to the present embodiment includes one or two or more collimators that selectively let the X-rays output from the X-ray sources through, the image processing apparatus according to the present embodiment controls, for example, the X-rays that pass through a collimator by changing the position of the collimator.

Figure 8:
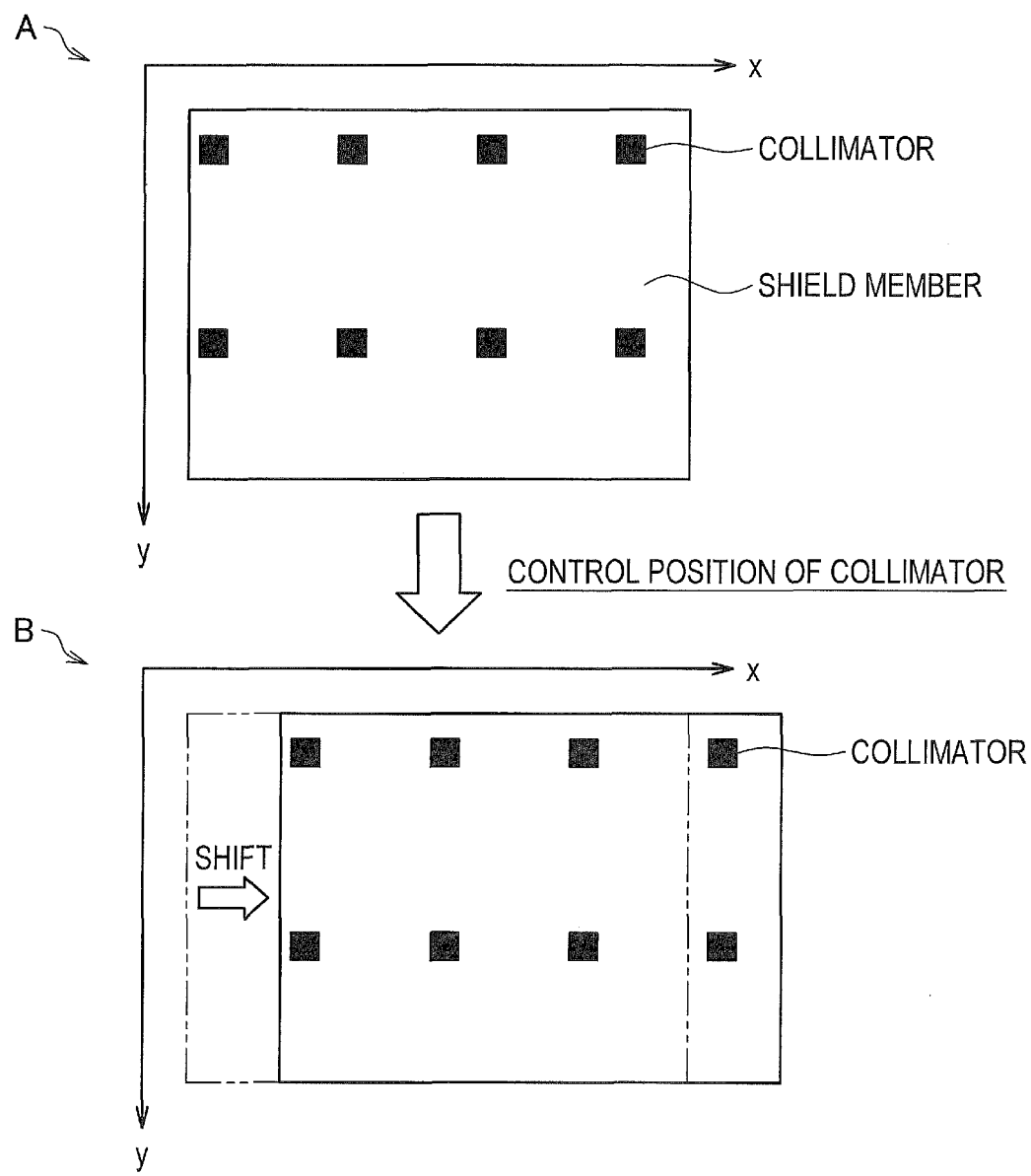
FIG. 8 is an explanatory diagram illustrating a third example of ray source control processing according to an embodiment of the present disclosure.

FIG. 6 is an explanatory diagram illustrating a third example of the ray source control processing according to the present embodiment. Here, FIG. 8A illustrates an example of a state of the collimator according to the present embodiment at a first time point, and FIG. 8B illustrates an example of a state of the collimator according to the present embodiment at a second time point (a time point after the first time point). It is noted that although FIG. 8 illustrates an example in which eight collimators are provided on the shield member blocking the X-rays, the number of collimators included in the ray source according to the present embodiment is not limited to eight. For example, one or two or more collimators may be provided for the collimator included in the ray source according to the present embodiment.

For example, as illustrated in FIGS. 8A and 8B, the image processing apparatus according to the present embodiment controls the position where the X-rays are let through (the position where the X-rays pass through the collimator) by moving the position of the collimators included in the ray source according to the present embodiment to shift their position. Here, for example, the image processing apparatus according to the present embodiment moves the position of the collimators included in the ray source according to the present embodiment in a horizontal direction, for example, by controlling an electric motor or a drive device in an arbitrary configuration that uses air pressure or hydraulic pressure. It is noted that the image processing apparatus according to the present embodiment may also move the position of the collimators included in the ray source according to the present embodiment in various directions, such as a vertical direction. The above-mentioned drive device may be included in the ray source according to the present embodiment, or be a separate device to the ray source according to the present embodiment.

Therefore, the image processing apparatus according to the present embodiment can acquire from the above-described detector a plurality of X-ray images that are based on X-ray detection data representing each detection result obtained by detecting a plurality of times in a time-division manner, and perform the processing (composite processing) of (I) on the plurality of acquired X-ray images.

The image processing apparatus according to the present embodiment performs any one of the processing operations according to the above-described first to third examples, for example, as (II) ray source control processing according to the present embodiment.

Here, due to the image processing apparatus according to the present embodiment performing the processing according to the above-described first to third examples, for example, the center position at which the X-rays are detected by the detector, such as the detector included in a below-described detection apparatus according to the present embodiment, changes.

Figure 9:
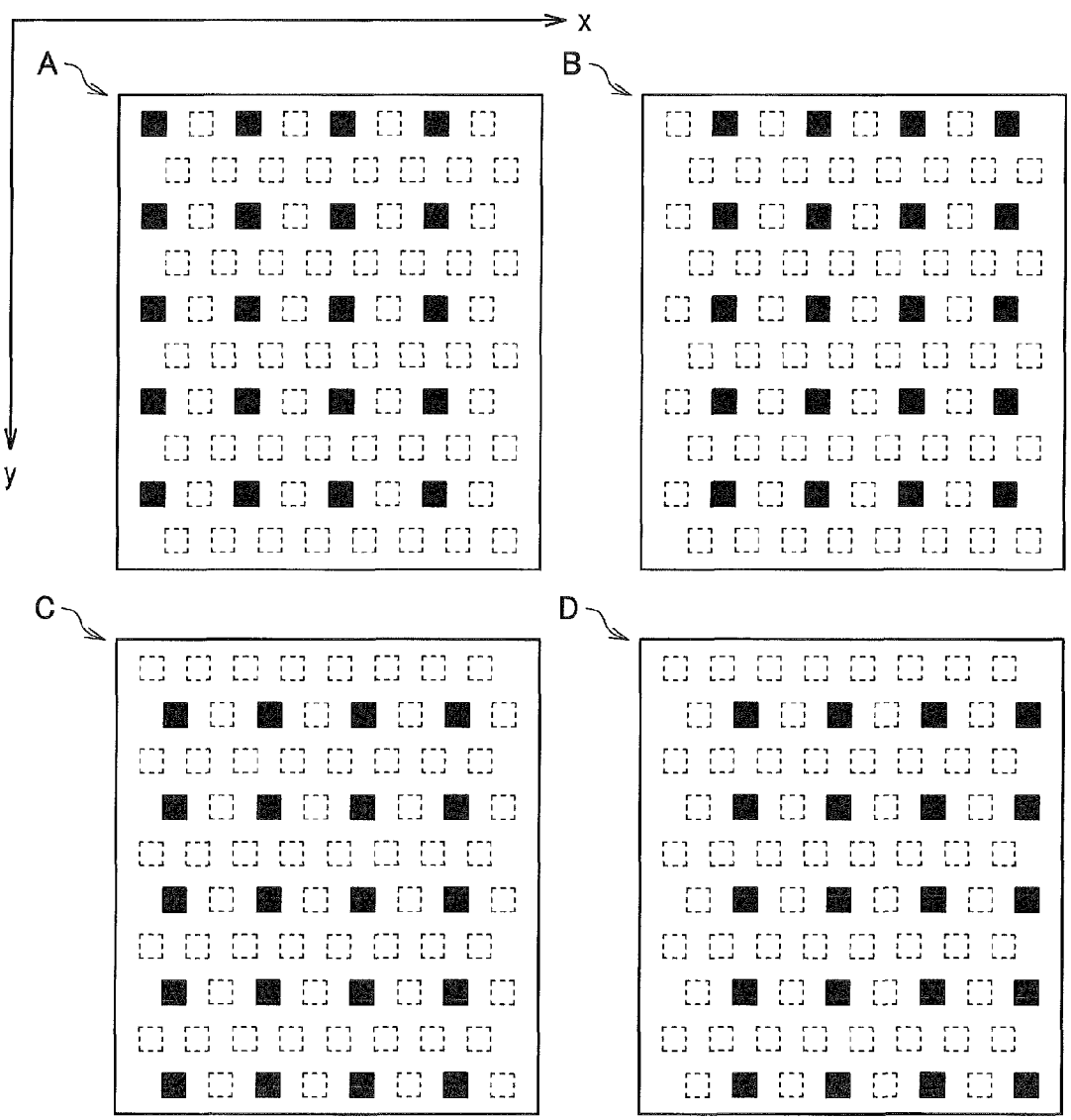
FIG. 9 is an explanatory diagram illustrating an example of processing performed in an image processing method according to an embodiment of the present disclosure.

FIG. 9 is an explanatory diagram illustrating an example of processing performed in the image processing method according to the present embodiment, which illustrates an example of the center position at which the X-rays detected by the detector are detected. Here, FIG. 9 illustrates examples in which X-rays are detected four times in a time-division manner at a detector by the image processing apparatus according to the present embodiment performing the processing (ray source control processing) of (II). Further, FIG. 9A illustrates an example of the detection result corresponding to FIG. 3A, and FIGS. 9B to 9D illustrate an example of the detection results corresponding to FIGS. 3B to 3D, respectively.

As illustrated in FIG. 9, due to a plurality of X-rays being detected in a time-division manner at the detector, the image processing apparatus according to the present embodiment can acquire from the detector a plurality of X-ray images that are based on X-ray detection data representing each detection result obtained by detecting a plurality of times in a time-division manner. Further, as described above, the image processing apparatus according to the present embodiment can obtain an X-ray image corresponding to the target by performing the processing (composite processing) of (I) on the plurality of acquired X-ray images.

Therefore, even when the image processing apparatus according to the present embodiment also performs the processing (ray source control processing) of (II) as the processing performed in the image processing method according to the present embodiment, the image processing apparatus according to the present embodiment can improve the image quality of an X-ray image.

(2) Processing Performed in the Image Processing Method According to the Present Embodiment Next, the above-described processing performed in the image processing method according to the present embodiment will be described in more detail. In the following, an example is described in which, as illustrated in FIG. 3, the image processing apparatus according to the present embodiment obtains an X-ray image corresponding to the target by superimposing four X-ray images that are based on X-ray detection data representing each detection result obtained by detecting a plurality of times in a time-division manner. More specifically, in the following, an example is described in which, as illustrated in FIG. 3, the image processing apparatus according to the present embodiment obtains an X-ray image corresponding to the target by superimposing X-ray images representing the detection results illustrated in FIGS. 9A to 9D in a state in which a target is present.

It is noted that, as described above, the image processing apparatus according to the present embodiment may obtain an X-ray image corresponding to the target by superimposing two or more X-ray images that are based on X-ray detection data detected in a time-division manner, for example.

(1) First Example of the Processing Performed in the Image Processing Method According to the Present Embodiment The image processing apparatus according to the present embodiment obtains an X-ray image corresponding to the target by superimposing four X-ray images obtained by performing image capturing with X-rays four times, for example.

More specifically, the image processing apparatus according to the present embodiment adds together the four X-ray images as illustrated in the following Equation 1, for example, to obtain an X-ray image corresponding to the target. Here, "$P_a$" in Equation 1 represents the X-ray image captured at a first time point, corresponding to the detection result illustrated in FIG. 9A, for example. Further, "$P_b$" in Equation 1 represents the X-ray image captured at a second time point (a time point after the first time point), corresponding to the detection result illustrated in FIG. 9B, for example. In addition, "$P_c$" in Equation 1 represents the X-ray image captured at a third time point (a time point after the second time point), corresponding to the detection result illustrated in FIG. 9C, for example. Moreover, "$P_d$" in Equation 1 represents the X-ray image captured at a fourth time point (a time point after the third time point), corresponding to the detection result illustrated in FIG. 9D, for example. Still further, (x,y) in Equation 1 represents a two-dimensional coordinate of the X-ray image based on an arbitrary position (e.g., the bottom left or the top right etc.) of the X-ray image as an origin.

$$O(x,y)=P_a(x,y)+P_b(x,y)+P_c(x,y)+P_d(x,y) \quad \text{(Equation 1)}$$

It is noted that as illustrated in FIG. 1, for example, X-ray diffusion can still occur even if each of the X-ray sources included in the ray source according to the present embodiment outputs parallel beam X-rays. Therefore, at the ray source according to the present embodiment, the X-ray source interval or the collimator interval are adjusted so that the total X-ray intensity obtained by summing at each position (x,y) is uniform while taking into consideration the diffusion range of the X-rays output from each X-ray source.

(2) Second Example of the Processing Performed in the Image Processing Method According to the Present Embodiment An X-ray image corresponding to the target can be obtained by adding four X-ray images as illustrated in Equation 1, for example. Further, as described above, the X-ray intensity in the X-ray image corresponding to the target can be made uniform by adjusting the ray source interval or the collimator interval in the ray source according to the present embodiment. Therefore, the image quality of the X-ray image can be improved by performing the processing performed in the image processing method according to the present embodiment.

However, unevenness in the X-ray intensity of the X-ray image corresponding to the target can still occur even if four X-ray images are simply added as illustrated in Equation 1, for example. However, if such unevenness in the X-ray intensity of the X-ray image corresponding to the target can be decreased, then the image quality of the X-ray image can be improved even further.

Accordingly, the image processing apparatus according to the present embodiment corrects the X-ray intensity of a plurality of X-ray images (hereinafter, sometimes referred to as "level correction") based on a plurality of calibration images corresponding to each of a plurality of X-ray images. Further, the image processing apparatus according to the present embodiment obtains an X-ray image corresponding to the target by superimposing the plurality of corrected X-ray images.

Here, the calibration images according to the present embodiment are X-ray images that are based on X-ray detection data representing each detection result in a state in which a target is not present, for example. For example, if four X-ray images based on X-ray detection data representing each detection result obtained by detecting four times in a time-division manner are the X-ray images representing the detection results illustrated in FIGS. 9A to 9D, each of the X-ray images representing the detection results illustrated in FIGS. 9A to 9D in a state in which the target is not present correspond to the calibration images according to the present embodiment.

If the calibration images representing the detection results illustrated in FIGS. 9A to 9D in a state in which the target is not present are "$C_a(x,y)$", "$C_b(x,y)$", "$C_c(x,y)$", and "$C_d(x,y)$", respectively, a calibration image $C(x,y)$ for correction that is used for the level correction according to the present embodiment can be expressed based on the following Equation 2, for example.

$$C(x,y)=C_a(x,y)+C_b(x,y)+C_c(x,y)+C_d(x,y) \quad \text{(Equation 2)}$$

Figure 10:
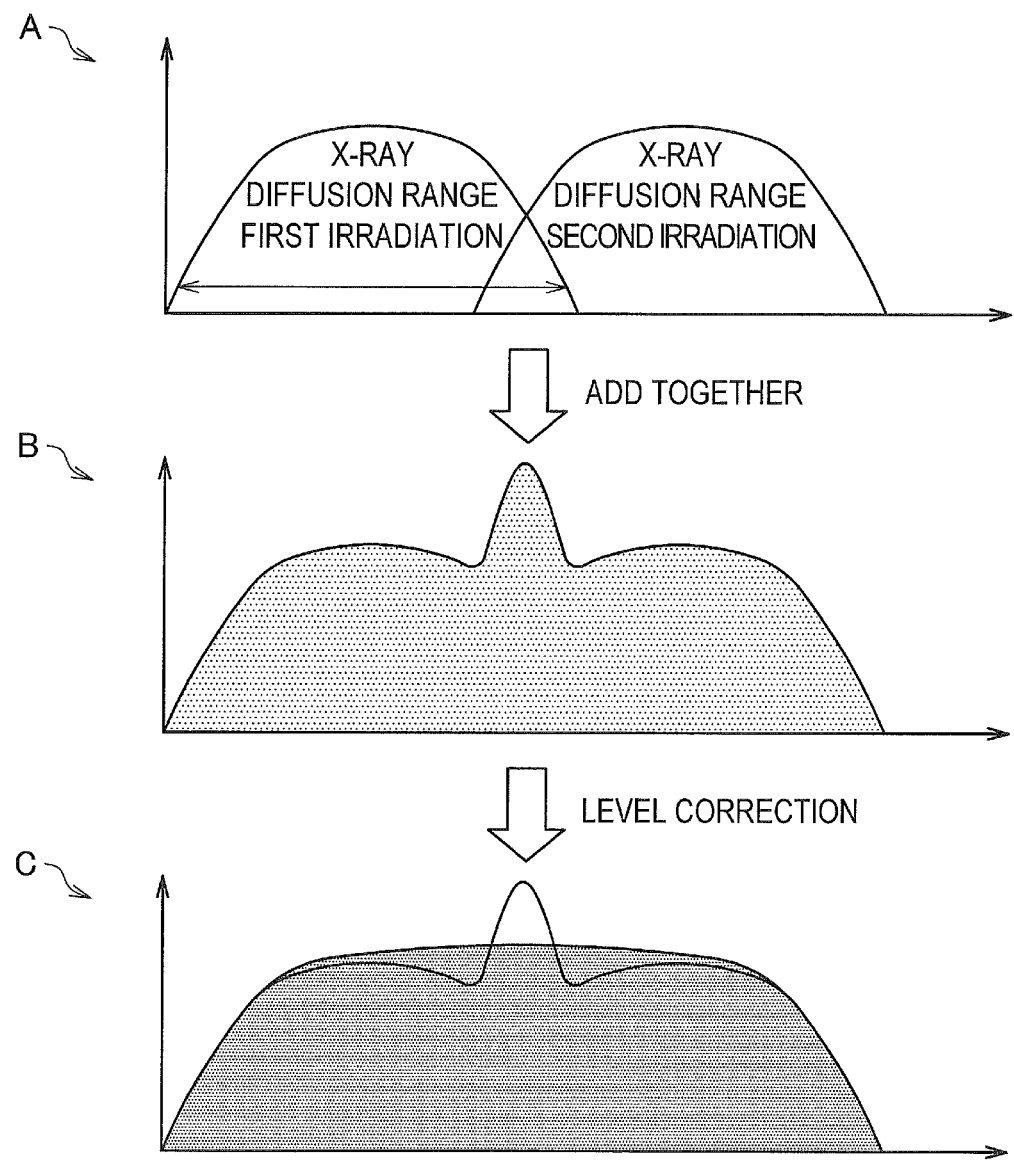
FIG. 10 is an explanatory diagram illustrating an example of processing performed in an image processing method according to an embodiment of the present disclosure.

FIG. 10 is an explanatory diagram illustrating an example of the processing performed in the image processing method according to the present embodiment, which illustrates an outline of the processing performed in the image processing method according to the second example. Here, in FIG. 10, an example is illustrated that adds together an X-ray image based on detection data of X-rays output at one time point (e.g., the first time X-rays were irradiated) from one X-ray source included in the ray source according to the present embodiment and an X-ray image based on detection data of X-rays output at another time point (e.g., the second time X-rays were irradiated) from another X-ray source included in the ray source according to the present embodiment. Further, in FIGS. 10A to 10C, the horizontal axis represents the position of the X-ray image, and the vertical axis represents the X-ray intensity.

For example, if X-ray images with an X-ray intensity like that illustrated in FIG. 10A are obtained, when these X-ray images are added together, localized unevenness like that illustrated in FIG. 10B can occur. Accordingly, the image processing apparatus according to the present embodiment prevents the occurrence of localized unevenness like that illustrated in FIG. 10C, for example, by performing level correction using a calibration image.

Therefore, the image processing apparatus according to the present embodiment can improve the image quality of the X-ray image even further by reducing the unevenness in the X-ray intensity of the X-ray image corresponding to the target.

More specifically, the image processing apparatus according to the present embodiment obtains an X-ray image $O(x,y)$ corresponding to the target by performing level correction based on the following Equation 3, for example. Here, "A" in Equation 3 is a constant for level adjustment. The constant for level adjustment according to the present embodiment may be, for example, a pre-set fixed value, or may be a variable value capable of being adjusted by a user operation and the like.

$$O(x,y)=A\times(P_a(x,y)+P_b(x,y)+P_c(x,y)+P_d(x,y))/C(x,y) \quad \text{(Equation 3)}$$

It is noted that, although an example is illustrated in which, in Equation 3, the image processing apparatus according to the present embodiment performs level correction using the calibration image C(x,y) for correction expressed in the above-described Equation 2, the processing performed in the image processing method according to the present embodiment is not limited to this. For example, the image processing apparatus according to the present embodiment can perform level correction using the calibration images $C_a(x,y)$, $C_b(x,y)$, $C_a(x,y)$, and $C_d(x,y)$ according to the present embodiment (i.e., calculate by substituting the above-described Equation 2 in for Equation 3).

FIG. 11 is an explanatory diagram illustrating an example of the processing performed in the image processing method according to the present embodiment, which illustrates an example of the processing performed in the image processing method according to the second example.

The image processing apparatus according to the present embodiment generates a calibration image C(x,y) for correction based on a plurality of calibration images (hereinafter sometimes referred to as "no-target X-ray captured image"), which are X-ray images obtained by capturing an image in a state in which a target is not present (S100). Here, the image processing apparatus according to the present embodiment performs the processing of step S100 by, for example, performing the calculation in the above-described Equation 2.

The image processing apparatus according to the present embodiment obtains an X-ray image on which level correction has been performed (hereinafter sometimes referred to as "output X-ray image") corresponding to the target based on X-ray images obtained by capturing an image in a state in which a target is present (hereinafter sometimes referred to as "target X-ray captured image") and the calibration image C(x,y) for correction generated in step S100 (S102). Here, the image processing apparatus according to the present embodiment performs the processing of step S102 by, for example, performing the calculation in the above-described Equation 3.

The image processing apparatus according to the present embodiment can obtain an X-ray image on which level correction has been performed corresponding to the target by, for example, performing the processing illustrated in FIG. 11.

(3) Third Example of the Processing Performed in the Image Processing Method According to the Present Embodiment Unevenness in the X-ray intensity can occur due to, for example, unevenness in the detection level at the detector detecting the parallel beam X-rays output from the ray source according to the present embodiment in the X-ray image corresponding to the target. Here, examples of such detection level unevenness include unevenness produced by missing pixels in the detector, such as a FPD, and unevenness produced at the joining portion when detectors, such as a FPD, are used together. However, if such X-ray intensity unevenness in the X-ray image corresponding to the target can be decreased, then the image quality of the X-ray image can be improved even further.

Accordingly, in addition to the calibration image according to the present embodiment, the image processing apparatus according to the present embodiment corrects the X-ray intensity of a plurality of X-ray images based on an offset image. Further, the image processing apparatus according to the present embodiment obtains an X-ray image corresponding to the target by superimposing a plurality of corrected X-ray images.

Here, the offset image according to the present embodiment is an X-ray image that is based on X-ray detection data in a state in which a target is not present and in which X-rays from the ray source according to the present embodiment have not been output. In the following, the offset image according to the present embodiment is sometimes referred to as "Q(x,y)".

More specifically, the image processing apparatus according to the present embodiment obtains an X-ray image O(x,y) corresponding to the target by performing level correction based on the following Equation 4, for example. Here, "A" in Equation 4 is a constant for level adjustment.

$$O(x,y)=A\times\{(P_a(x,y)+P_b(x,y)+P_c(x,y)+P_d(x,y)-4Q(x,y))/C(x,y)-4Q(x,y)\} \quad \text{(Equation 4)}$$

It is noted that, although an example is illustrated in which, in Equation 4, the image processing apparatus according to the present embodiment performs level correction using the calibration image C(x,y) for correction expressed in the above-described Equation 2, the processing performed in the image processing method according to the present embodiment is not limited to this. For example, the image processing apparatus according to the present embodiment can perform level correction using the calibration images $C_a(x,y)$, $C_b(x,y)$, $C_a(x,y)$, and $C_d(x,y)$ according to the present embodiment (i.e., calculate by substituting the above-described Equation 2 in for Equation 4).

FIG. 12 is an explanatory diagram illustrating an example of the processing performed in the image processing method according to the present embodiment, which illustrates an example of the processing performed in the image processing method according to the third example.

Similar to step S100 in FIG. 11, the image processing apparatus according to the present embodiment generates a calibration image for correction based on a plurality of calibration images obtained by capturing an image in a state in which a target is not present (S200).

The image processing apparatus according to the present embodiment obtains an X-ray image on which level correction has been performed corresponding to the target based on X-ray images obtained by capturing an image in a state in which a target is present, the calibration image C(x,y) for correction generated in step S200, and the offset image Q(x,y) (S202). Here, the image processing apparatus according to the present embodiment performs the processing of step S202 by, for example, performing the calculation in the above-described Equation 4.

The image processing apparatus according to the present embodiment can obtain an X-ray image on which level correction has been performed corresponding to the target by, for example, performing the processing illustrated in FIG. 12.

(4) Fourth Example of the Processing Performed in the Image Processing Method According to the Present Embodiment As described above, in the processing (composite processing) of (I), the image processing apparatus according to the present embodiment superimposes a plurality of X-ray images that are based on X-ray detection data representing each detection result obtained by detecting a plurality of times in a time-division manner at a detector.

Here, if, for example, the target moves during the midst of the plurality of X-rays being detected at the detector (a case in which the target has moved while an image is being captured with X-rays), a positional deviation is produced in the position of the target among the plurality of obtained X-ray images. Further, when a plurality of images in which such positional deviation has occurred are superimposed, unevenness in the X-ray intensity in an X-ray image corresponding to the target can occur due to the positional deviation. However, if such unevenness in the X-ray intensity of the X-ray image corresponding to the target can be decreased, then the image quality of the X-ray image can be improved even further.

Accordingly, the image processing apparatus according to the present embodiment corrects a detected positional deviation among the X-ray images based on a detection result of positional deviation among a plurality of X-ray images that are based on X-ray detection data representing each detection result obtained by detecting a plurality of times in a time-division manner. Further, the image processing apparatus according to the present embodiment obtains an X-ray image corresponding to the target by superimposing the plurality of images in which positional deviation has been corrected.

Here, the processing relating to the detection of positional deviation among a plurality of X-ray images according to the present embodiment can be carried out by the image processing apparatus according to the present embodiment, or by an external apparatus, for example. When the processing relating to the detection of positional deviation among a plurality of X-ray images according to the present embodiment is carried out by an external apparatus, the image processing apparatus according to the present embodiment corrects the positional deviation among the X-ray images using data representing a detection result of positional deviation acquired from that external apparatus. In the following, the processing performed in the image processing method according to the present embodiment will be described based on an example in which the image processing apparatus according to the present embodiment performs the processing relating to the detection of positional deviation among a plurality of X-ray images according to the present embodiment.

FIG. 13 is an explanatory diagram illustrating an example of the processing performed in the image processing method according to the present embodiment, which illustrates an outline of the processing performed in the image processing method according to the fourth example. Here, in FIG. 10, an example is illustrated in which the processing performed in the image processing method according to the fourth example is performed on an X-ray image that is based on detection data of X-rays output at one time point (e.g., the first time X-rays were irradiated) from one X-ray source included in the ray source according to the present embodiment and an X-ray image that is based on detection data of X-rays output at another time point (e.g., the second time X-rays were irradiated) from another X-ray source included in the ray source according to the present embodiment.

As illustrated in FIG. 13, for example, the image processing apparatus according to the present embodiment superimposes a plurality of X-ray images after having corrected the positional deviation of the X-ray images.

More specifically, based on one image as a reference image among a plurality of X-ray images that are based on X-ray detection data representing each detection result obtained by detecting a plurality of times in a time-division manner at a detector, for example, the image processing apparatus according to the present embodiment corrects a deviation amount of the other images. In the following, an example will be described in which, based on an X-ray image "$P_a(x,y)$" corresponding to the detection result of FIG. 9 as the reference image, the image processing apparatus according to the present embodiment corrects the positional deviation of X-ray images "$P_b(x,y)$", "$P_c(x,y)$", and "$P_d(x,y)$" corresponding to the detection results of FIGS. 9B to 9D.

Here, the image processing apparatus according to the present embodiment detects a deviation amount of the other X-ray images with respect to the reference image by, for example, using an arbitrary method that is capable of detecting a deviation amount among images, such as matching processing that utilizes a motion vector detection method.

Figure 14:
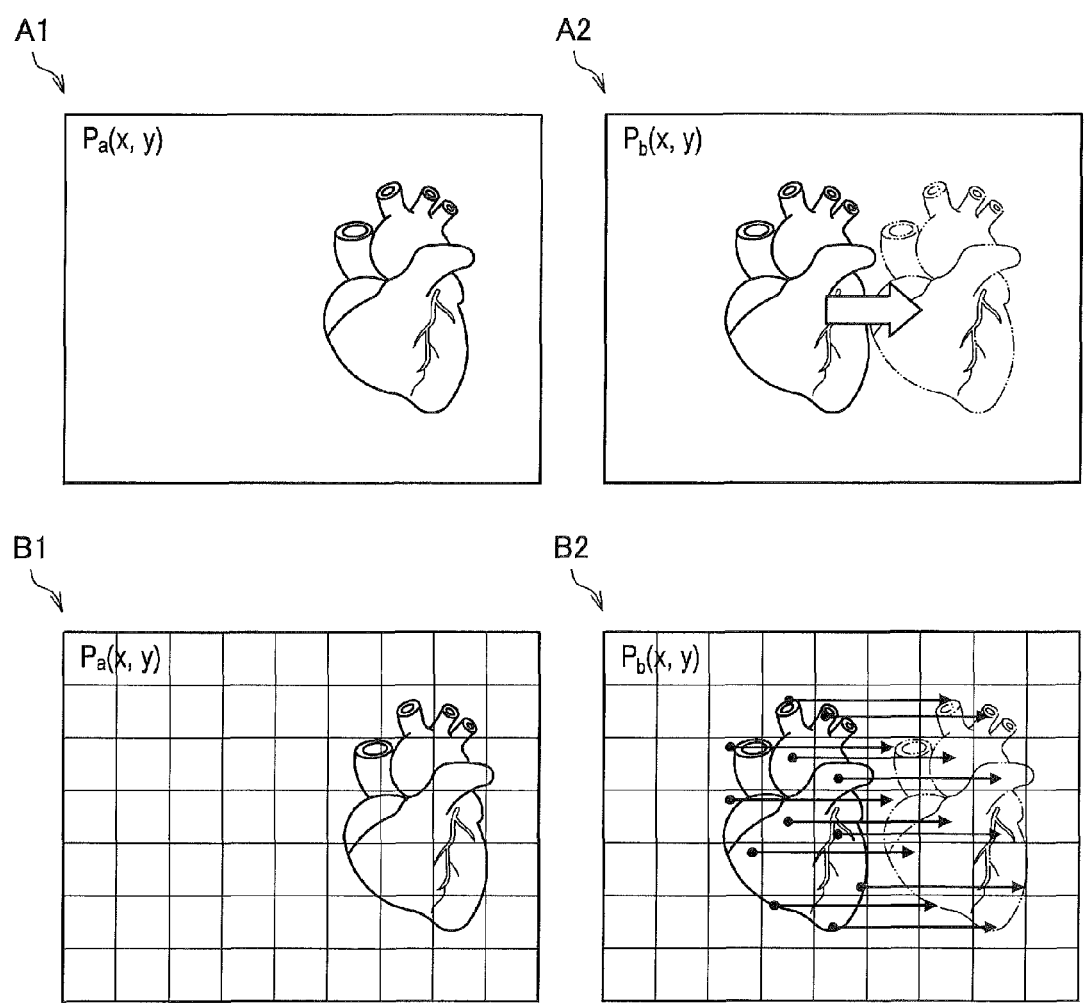
FIG. 14 is an explanatory diagram illustrating an example of processing performed in an image processing method according to an embodiment of the present disclosure.

FIG. 14 is an explanatory diagram illustrating an example of the processing performed in the image processing method according to the present embodiment, which illustrates an example of processing relating to the detection of a deviation amount of other images with respect to a reference image according to the present embodiment.

For example, as illustrated in FIGS. 14A1 and 14A2, the image processing apparatus according to the present embodiment can detect the deviation amount of the other X-ray images with respect to the reference image by performing whole screen matching that detects one deviation amount in whole screen units. Further, as illustrated in FIGS. 14B1 and 14B2, the image processing apparatus according to the present embodiment can also detect the deviation amount of the other X-ray images with respect to the reference image by dividing the reference image and the other images into respective blocks (divided areas), and performing block matching that detects a motion vector for each block. In addition, the image processing apparatus according to the present embodiment can also detect the deviation amount of the other X-ray images with respect to the reference image by detecting a motion vector in pixel units in the reference image and the other images, for example.

Further, the image processing apparatus according to the present embodiment obtains the X-ray image $O(x,y)$ corresponding to the target by performing positional deviation correction based on the following Equation 5, for example. Here, "$(dx_b, dy_b)$" in Equation 5 represents the positional deviation amount of the other X-ray image $P_b(x,y)$ with respect to the reference image $P_a(x,y)$. Further, "$(dx_c, dy_c)$" in Equation 5 represents the positional deviation amount of the other X-ray image $P_b(x,y)$ with respect to the reference image $P_a(x,y)$, and "$(dx_d, dy_d)$" in Equation 5 represents the positional deviation amount of the other X-ray image $P_d(x,y)$ with respect to the reference image $P_a(x,y)$.

$$O(x,y)=P_a(x,y)+P_b(x-dx_b,y-dy_b)+P_c(x-dx_c,y-dy_c)+P_d(x-dx_d,y-dy_d) \quad \text{(Equation 5)}$$

Figure 15:
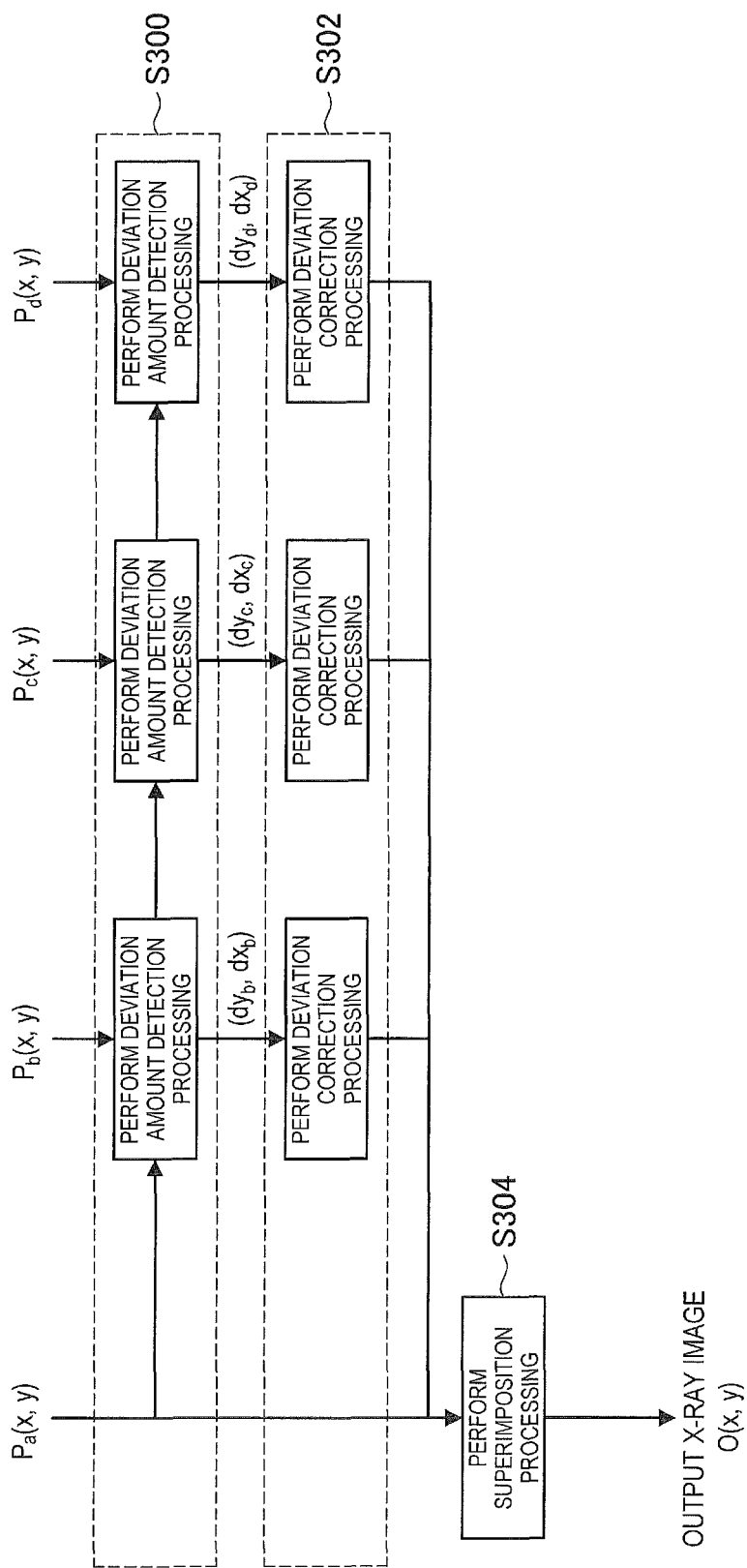
FIG. 15 is an explanatory diagram illustrating an example of processing performed in an image processing method according to an embodiment of the present disclosure.

FIG. 15 is an explanatory diagram illustrating an example of the processing performed in the image processing method according to the present embodiment, which illustrates an example of the processing performed in the image processing method according to the fourth example.

The image processing apparatus according to the present embodiment detects a positional deviation amount of the other X-ray images $P_b(x,y)$, $P_b(x,y)$, and $P_d(x,y)$, respectively, with respect to the reference image $P_a(x,y)$ (S300). The image processing apparatus according to the present embodiment performs the processing of step S300 by, for example, using an arbitrary method that is capable of detecting a deviation amount among images, such as matching processing.

The image processing apparatus according to the present embodiment corrects the positional deviation of each of the other X-ray images $P_b(x,y)$, $P_b(x,y)$, and $P_d(x,y)$ based on the deviation amounts detected in step S300 (S302). The image processing apparatus according to the present embodiment performs the processing of step S302 by, for example, subtracting the detected corresponding deviation amount from each of the other X-ray images $P_b(x,y)$, $P_b(x,y)$, and $P_d(x,y)$.

The image processing apparatus according to the present embodiment can obtain an X-ray image corresponding to the target in which positional deviation has been corrected by performing the processing illustrated in FIG. 15, for example.

(5) Fifth Example of the Processing Performed in the Image Processing Method According to the Present Embodiment The processing performed in the image processing method according to the present embodiment is not limited to the processing performed in the above-described image processing methods according to the first to fourth examples. For example, in the processing performed in the image processing method according to the second example, the image processing apparatus according to the present embodiment can correct the positional deviation of a plurality of X-ray images that are based on X-ray detection data representing each detection result obtained by detecting a plurality of times in a time-division manner, and each of a plurality of calibration images corresponding to the plurality of X-ray images.

As described above, if, for example, the target moves during the midst of the plurality of X-rays being detected at the detector (a case in which the target has moved while an image is being captured with X-rays), a positional deviation is produced in the position of the target among the obtained plurality of X-ray images. However, the image quality of the X-ray image can be improved further by, like in the processing performed in the image processing method according to the fourth example, correcting the detected positional deviation among the X-ray images and superimposing the plurality of X-ray images in which positional deviation has been corrected.

In addition, like in the processing performed in the image processing method according to the second example, when correcting the X-ray intensity of a plurality of X-ray images that are based on X-ray detection data representing each detection result obtained by detecting a plurality of times in a time-division manner based on the calibration image C(x,y) for correction, positional deviation can occur between the plurality of X-ray images and the calibration image, for example, due to the correction of positional deviation among the detected X-ray images. Further, when such positional deviation has occurred, unevenness in the X-ray intensity of the X-ray images corresponding to the target can occur due to the positional deviation.

However, if such X-ray intensity unevenness in the X-ray image corresponding to the target can be decreased, then the image quality of the X-ray image can be improved even further.

Accordingly, the image processing apparatus according to the present embodiment corrects the positional deviation of a plurality of calibration images based on a detection result of positional deviation among a plurality of X-ray images that are based on X-ray detection data representing each detection result obtained by detecting a plurality of times in a time-division manner. Further, the image processing apparatus according to the present embodiment corrects the X-ray intensity of the plurality of X-ray images in which positional deviation has been corrected based on the plurality of calibration images in which positional deviation has been corrected. In addition, the image processing apparatus according to the present embodiment obtains an X-ray image corresponding to the target by superimposing the plurality of corrected images.

Here, the image processing apparatus according to the present embodiment corrects the positional deviation among the plurality of calibration images by, similar to the correction of positional deviation among the plurality of X-ray images that are based on X-ray detection data representing each detection result obtained by detecting a plurality of times in a time-division manner, for example, using an arbitrary method that is capable of detecting a deviation amount among images, such as matching processing that utilizes a motion vector detection method.

The calibration image C(x,y) for correction in which positional deviation has been corrected is expressed by, for example, the following Equation 6. Here, "$(dx_b,dy_b)$" in Equation 6 represents the positional deviation amount of the other X-ray image $P_b(x,y)$ with respect to the reference image $P_a(x,y)$. Further, "$(dx_c,dy_c)$" in Equation 6 represents the positional deviation amount of the other X-ray image $P_b(x,y)$ with respect to the reference image $P_a(x,y)$, and "$(dx_d,dy_d)$" in Equation 6 represents the positional deviation amount of the other X-ray image $P_d(x,y)$ with respect to the reference image $P_a(x,y)$.

$$C'(x,y)=C_a(x,y)+C_b(x-dx_b,y-dy_b)+C_c(x-dx_c,y-dy_c)+C_d(x-dx_d,y-dy_d) \quad \text{(Equation 6)}$$

More specifically, the image processing apparatus according to the present embodiment obtains the X-ray image O(x,y) corresponding to the target by performing level correction having corrected, based on the following Equation 7, for example, the positional deviation among a plurality of X-ray images that are based on X-ray detection data representing each detection result obtained by detecting a plurality of times in a time-division manner, and corrected the positional deviation among a plurality of calibration images. Here, "$(dx_b,dy_b)$" in Equation 5 represents the positional deviation amount of the other X-ray image $P_b(x,y)$ with respect to the reference image $P_a(x,y)$. Further, "$(dx_c,dy_c)$" in Equation 5 represents the positional deviation amount of the other X-ray image $P_b(x,y)$ with respect to the reference image $P_a(x,y)$, and "$(dx_d,dy_d)$" in Equation 5 represents the positional deviation amount of the other X-ray image $P_d(x,y)$ with respect to the reference image $P_a(x,y)$.

$$O(x,y)=A\times(P_a(x,y)+P_b(x-dx_b,y-dy_b)+P_c(x-dx_c,y-dy_c)+P_d(x-dx_d,y-dy_d))/C'(x,y) \quad \text{(Equation 7)}$$

It is noted that, although an example is illustrated in which, in Equation 7, the image processing apparatus according to the present embodiment performs level correction and the like using the calibration image C'(x,y) for correction expressed in the above-described Equation 6, the processing performed in the image processing method according to the present embodiment is not limited to this. For example, the image processing apparatus according to the present embodiment can perform level correction using the calibration images $C_a(x,y)$, $C_b(x,y)$, $C_c(x,y)$, and $C_d(x,y)$ according to the present embodiment (i.e., calculate by substituting the above-described Equation 6 in for Equation 7).

Figure 16:
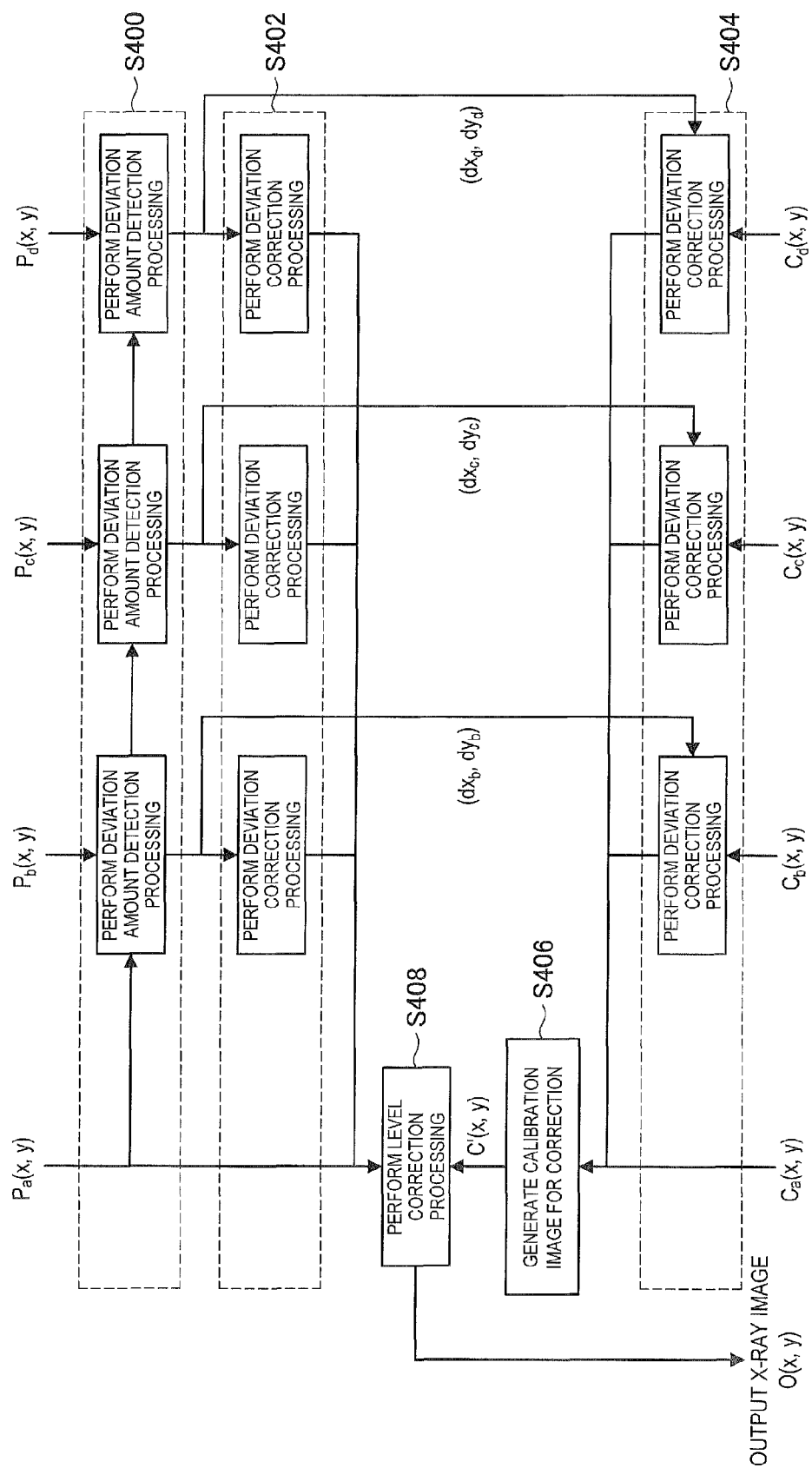
FIG. 16 is an explanatory diagram illustrating an example of processing performed in an image processing method according to an embodiment of the present disclosure.

FIG. 16 is an explanatory diagram illustrating an example of the processing performed in the image processing method according to the present embodiment, which illustrates an example of the processing performed in the image processing method according to the fifth example.

Similar to in step S300 in FIG. 15, the image processing apparatus according to the present embodiment detects a positional deviation amount of the other X-ray images $P_b(x,y)$, $P_c(x,y)$, and $P_d(x,y)$, respectively, with respect to the reference image $P_a(x,y)$ (S400).

Similar to step S302 in FIG. 15, the image processing apparatus according to the present embodiment corrects the positional deviation of each of the other X-ray images $P_b(x,y)$, $P_c(x,y)$, and $P_d(x,y)$ based on the deviation amounts detected in step S400 (S402).

The image processing apparatus according to the present embodiment corrects the positional deviation of each of the calibration images $C_b(x,y)$, $C_a(x,y)$, and $C_d(x,y)$ other than the calibration image corresponding to the reference image, for example, based on the deviation amounts detected in step S400 (S404). Here, the image processing apparatus according to the present embodiment performs the processing of step S404 by, for example, subtracting the detected corresponding deviation amount from each of the calibration images $C_b(x,y)$, $C_b(x,y)$, and $C_d(x,y)$ other than the calibration image corresponding to the reference image, for example.

The image processing apparatus according to the present embodiment generates a calibration image for correction based on the plurality of calibration images obtained whose positional deviation was corrected in step S404 (S406). Here, the image processing apparatus according to the present embodiment performs the processing of step S406 by, for example, performing the calculation in the above-described Equation 6, for example.

The image processing apparatus according to the present embodiment obtains an X-ray image corresponding to the target in which level correction has been performed based on X-ray images obtained by capturing an image in a state in which a target is present whose positional deviation was corrected in step S402, and the calibration image C'(x,y) for correction generated in step S406 (S408). Here, the image processing apparatus according to the present embodiment performs the processing of step S408 by, for example, performing the calculation in the above-described Equation 7.

The image processing apparatus according to the present embodiment can obtain an X-ray image corresponding to the target in which positional deviation correction and level correction have been performed by, for example, performing the processing illustrated in FIG. 16.

(6) Sixth Example of the Processing Performed in the Image Processing Method According to the Present Embodiment The processing performed in the image processing method according to the present embodiment is not limited to the processing performed in the above-described image processing methods according to the first to fifth examples. For example, in the processing performed in the image processing method according to the fourth example, and the processing performed in the image processing method according to the fifth example, respectively, the image processing apparatus according to the present embodiment can also perform X-ray intensity correction based on a calibration image for a plurality of X-ray images that are based on X-ray detection data representing each detection result obtained by detecting a plurality of times in a time-division manner, and perform processing on the plurality of X-ray images whose X-ray intensity correction was corrected.

By performing processing on a plurality of X-ray images whose X-ray intensity has been corrected, the image processing apparatus according to the present embodiment can, with respect to a reference image, more accurately detect the deviation amount in the position of each of the other X-ray images. Therefore, since the image processing apparatus according to the present embodiment can correct positional deviation more accurately, the quality of the X-ray image can improved even further.

Here, examples of the processing relating to correction of the X-ray intensity on the plurality of X-ray images that are based on X-ray detection data representing each detection result obtained by detecting a plurality of times in a time-division manner in the processing performed in the image processing method according to the sixth example include the correction represented in the following Equation 8, for example. Here, "$P'_a(x,y)$" in Equation 8 represents the X-ray image obtained by correcting the X-ray intensity of the X-ray image $P_a(x,y)$. Further, "$P'_b(x,y)$", "$P'_c(x,y)$", and "$P'_d(x,y)$" in Equation 8 represent the X-ray images obtained by correcting the X-ray intensities of the X-ray images $P_b(x,y)$, $P_c(x,y)$, and $P_d(x,y)$, respectively.

$$\begin{cases} P'_a(x, y) = P_a(x, y) / C_a(x, y) \\ P'_b(x, y) = P_b(x, y) / C_b(x, y) \\ P'_c(x, y) = P_c(x, y) / C_c(x, y) \\ P'_d(x, y) = P_d(x, y) / C_d(x, y) \end{cases} \quad \text{(Equation 8)}$$

More specifically, the image processing apparatus according to the present embodiment obtains an X-ray image O(x,y) corresponding to the target based on the following Equation 9 or the following Equation 10, for example. Here, the image processing apparatus according to the present embodiment uses the following Equation 9 when, in the processing performed in the image processing method according to the above-described fourth example, performing X-ray intensity correction based on a calibration image for a plurality of X-ray images that are based on X-ray detection data representing each detection result obtained by detecting a plurality of times in a time-division manner, and performing processing on the plurality of X-ray images whose X-ray intensity was corrected. Further, the image processing apparatus according to the present embodiment uses the following Equation 10 when, in the processing performed in the image processing method according to the above-described fifth example, performing X-ray intensity correction based on a calibration image for a plurality of X-ray images that are based on X-ray detection data representing each detection result obtained by detecting a plurality of times in a time-division manner, and performing processing on the plurality of X-ray images whose X-ray intensity correction was performed.

$$O(x,y) = P_a(x,y) + P_b(x-dx_b, y-dy_b) + P_c(x-dx_c, y-dy_c) + P_d(x-dx_d, y-dy_d))/C'(x,y) \quad \text{(Equation 9)}$$

$$O(x,y) = A \times (P_a(x,y) + P_b(x-dx_b, y-dy_b) + P_c(x-dx_c, y-dy_c) + P_d(x-dx_d, y-dy_d))/C'(x,y) \quad \text{(Equation 10)}$$

Figure 17:
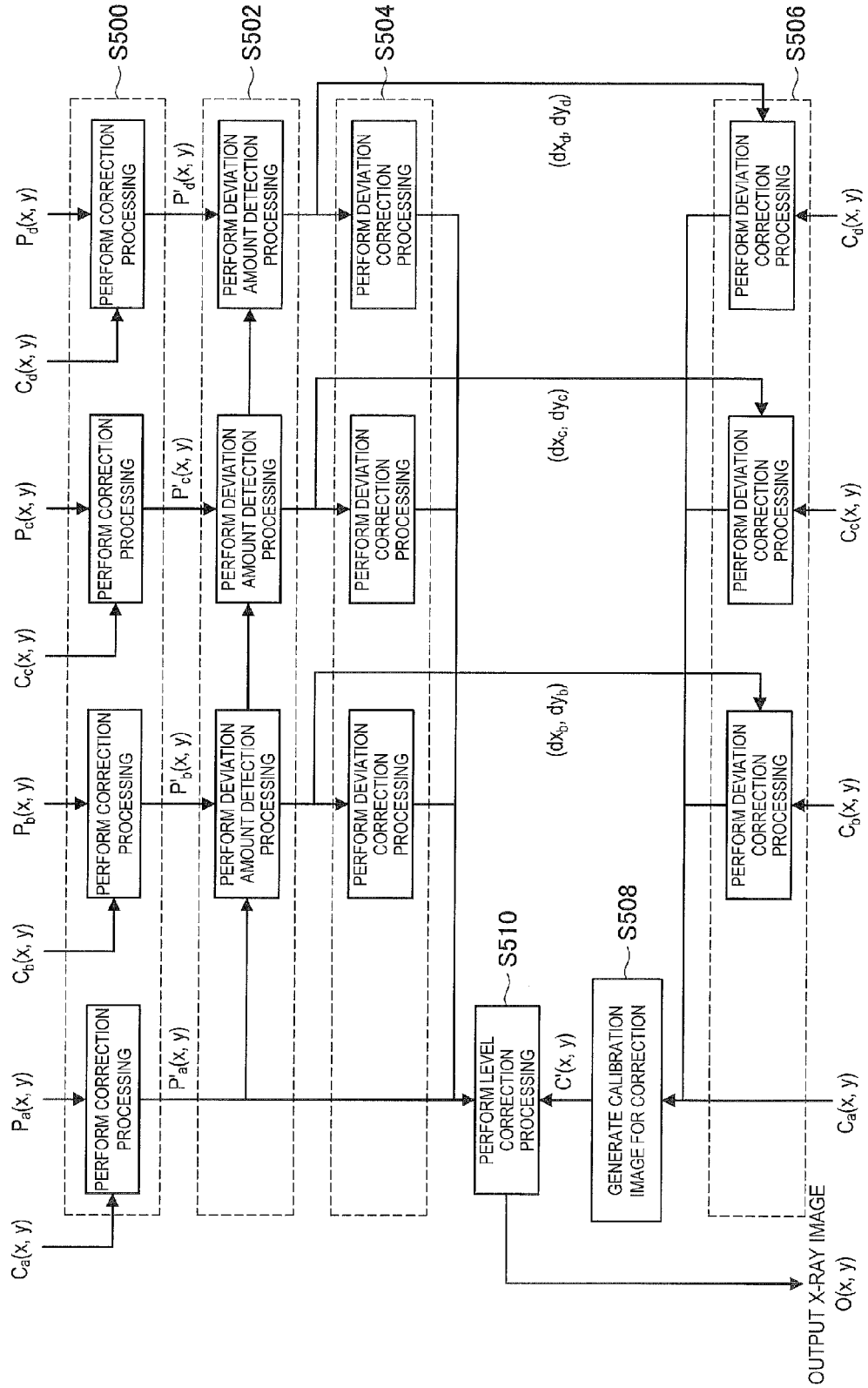
FIG. 17 is an explanatory diagram illustrating an example of processing performed in an image processing method according to an embodiment of the present disclosure.

FIG. 17 is an explanatory diagram illustrating an example of the processing performed in the image processing method according to the present embodiment, which illustrates an example of the processing performed in the image processing method according to the sixth example. Here, FIG. 17 illustrates an example of the processing performed by the image processing apparatus according to the present embodiment when, for example, in the processing performed in the image processing method according to the fifth example, performing X-ray intensity correction based on a calibration image for a plurality of X-ray images that are based on X-ray detection data representing each detection result obtained by detecting a plurality of times in a time-division manner, and performing processing on the plurality of X-ray images whose X-ray intensity was corrected.

The image processing apparatus according to the present embodiment performs X-ray intensity correction based on a calibration image $C_a(x,y)$ corresponding to a reference image $P_a(x,y)$ on a plurality of X-ray images $P_a(x,y)$, $P_b(x,y)$, $P_c(x,y)$, and $P_d(x,y)$, respectively, based on X-ray detection data representing each detection result obtained by detecting four times in a time-division manner (S500). Here, the image processing apparatus according to the present embodiment performs the processing of step S500 by, for example, performing the calculation in the above-described Equation 8.

Similar to in step S300 in FIG. 15, the image processing apparatus according to the present embodiment detects a positional deviation amount of the other X-ray images $P'_b(x,y)$, $P'_b(x,y)$, and $P'_d(x,y)$, respectively, with respect to the reference image $P'_a(x,y)$ (S502).

Similar to step S302 in FIG. 15, the image processing apparatus according to the present embodiment corrects the positional deviation of each of the other X-ray images $P_b(x,y)$, $P_a(x,y)$, and $P_d(x,y)$ based on the deviation amounts detected in step S502 (S504).

Similar to step S404 in FIG. 16, the image processing apparatus according to the present embodiment corrects the positional deviation of each of the calibration images $C_b(x,y)$, $C_a(x,y)$, and $C_d(x,y)$ other than the calibration image corresponding to the reference image, for example, based on the deviation amounts detected in step S502 (S506).

Similar to step S406 in FIG. 16, the image processing apparatus according to the present embodiment generates a calibration image for correction based on the plurality of calibration images obtained whose positional deviation was corrected in step S506 (S508).

The image processing apparatus according to the present embodiment obtains an X-ray image on which level correction has been performed corresponding to the target based on the X-ray images obtained by capturing an image in a state in which a target is present whose positional deviation was corrected in step S504, and the calibration image C'(x,y) for correction generated in step S508 (S510). Here, the image processing apparatus according to the present embodiment performs the processing of step S510 by, for example, performing the calculation in the above-described Equation 10.

The image processing apparatus according to the present embodiment can obtain an X-ray image corresponding to the target on which positional deviation correction and level correction have been performed by, for example, performing the processing illustrated in FIG. 17.

As the processing performed in the image processing method according to the present embodiment, the image processing apparatus according to the present embodiment performs the processing performed in any of the above-described first to sixth examples. The processing (composite processing) of (I) performed in the image processing method according to the present embodiment is realized no matter which of the processing operations performed in the above-described first to sixth examples is employed, for example.

Therefore, no matter which of the processing operations performed in the above-described first to sixth examples is employed, for example, the image processing apparatus according to the present embodiment can improve the image quality of an X-ray image.

It is noted that the processing performed in the image processing method according to the present embodiment is not limited to the processing performed in the image processing method according to the first to sixth examples. For example, the image processing apparatus according to the present embodiment can also perform the processing (ray source control processing) of (II) as well.

Figure 18:
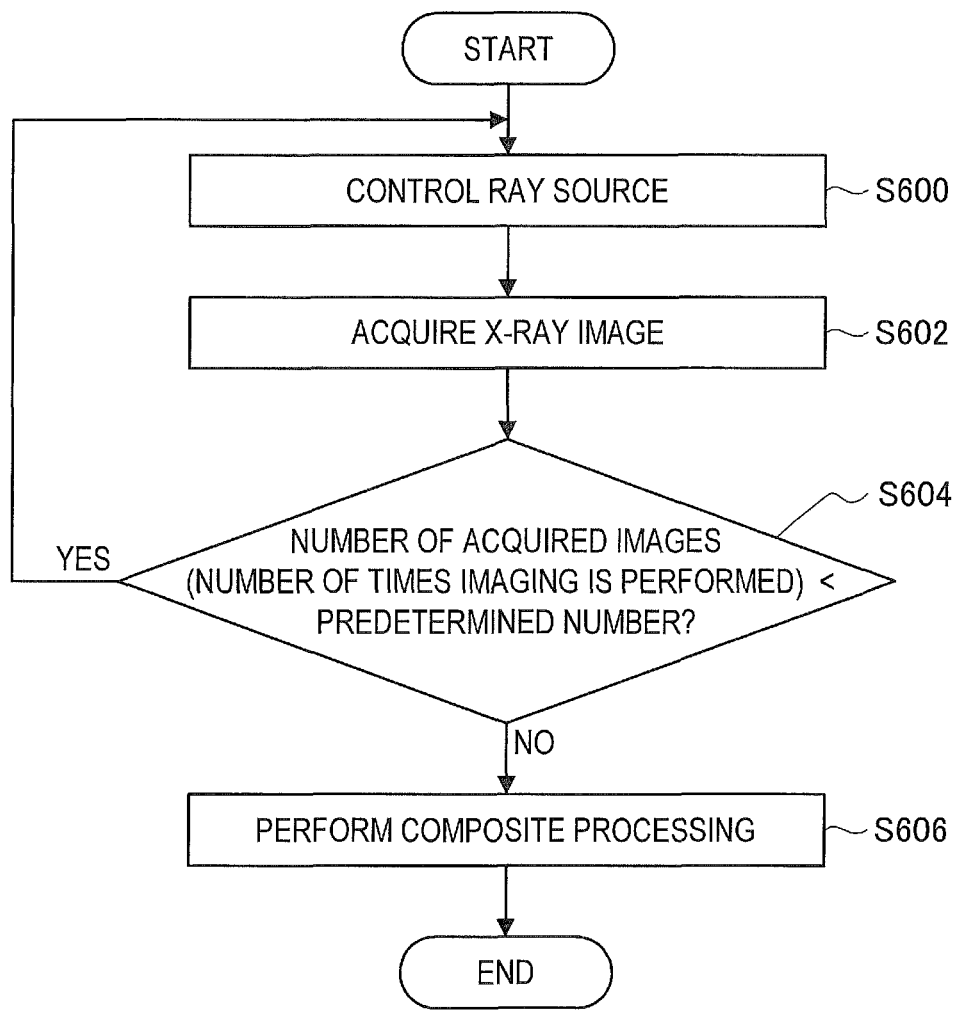
FIG. 18 is an explanatory diagram illustrating an example of processing performed in an image processing method according to an embodiment of the present disclosure.

FIG. 18 is an explanatory diagram illustrating an example of the processing performed in the image processing method according to the present embodiment, which illustrates another example of the processing performed in the image processing method according to the present embodiment. Here, the processing of S600 in FIG. 16 corresponds to the processing (ray source control processing) of (II), and the processing of S606 in FIG. 16 corresponds to the processing (composite processing) of (I).

The image processing apparatus according to the present embodiment performs image capturing with X-rays by controlling the ray source according to the present embodiment (S600). Here, the image processing apparatus according to the present embodiment performs the processing operations performed in any of the above-described (A) to (C) as the processing of step S600.

The image processing apparatus according to the present embodiment acquires the X-ray image obtained by the image capturing that was controlled based on the processing of step S600, from, for example, an apparatus that includes a detector (e.g., the below-described detection apparatus according to the present embodiment), or a detection unit (described below) that is included in the image processing apparatus according to the present embodiment (S602). Here, the image processing apparatus according to the present embodiment acquires the X-ray image that is based on X-ray detection data by receiving X-ray detection data that is mainly transmitted by the apparatus including the above-mentioned detector. However, the processing performed in step S602 is not limited to this. For example, the image processing apparatus according to the present embodiment can also acquire the X-ray image that is based on X-ray detection data by transmitting to the apparatus including the above-mentioned detector a transmission request requesting transmission of the X-ray detection data, and receiving the X-ray detection data that was transmitted in response to the transmission request.

When the X-ray image is acquired in step S602, the image processing apparatus according to the present embodiment determines whether the number of acquired X-ray images (corresponding to the number of times imaging was performed with X-rays) is less than a predetermined number of times, for example (S604). Here, this predetermined number of times may be a pre-set fixed value, or may be a variable value capable of being adjusted by a user operation and the like. If the predetermined number of times is changed, the image processing apparatus according to the present embodiment changes how the ray source is controlled in step S600 so as to match the set predetermined number of times.

If it is determined in step S604 that the number of acquired X-ray images is smaller than the predetermined number of times, the image processing apparatus according to the present embodiment repeats the processing from step S600.

Further, if it is determined in step S604 that the number of acquired X-ray images is not smaller than the predetermined number of times, the image processing apparatus according to the present embodiment performs composite processing (step S606). Here, the image processing apparatus according to the present embodiment performs the processing performed in any of the above-described first to sixth examples as the processing of step S606.

The image processing apparatus according to the present embodiment performs the above-described processing (composite processing) of (I) and the above-described processing (ray source control processing) of (II) by performing the processing illustrated in FIG. 18, for example. Therefore, the image processing apparatus according to the present embodiment can improve the image quality of an X-ray image by performing the processing illustrated in FIG. 18, for example.

(7) Seventh Example of the Processing Performed in the Image Processing Method According to the Present Embodiment The processing performed in the image processing method according to the present embodiment is not limited to the processing performed in the above-described image processing methods according to the first to sixth examples. For example, if a plurality of first X-ray images and a second X-ray image are included in the plurality of X-ray images according to the present embodiment that are based on X-ray detection data representing each detection result obtained by detecting a plurality of times in a time-division manner, the image processing apparatus according to the present embodiment can, for example, correct each of the plurality of first X-ray images based on the second X-ray image, and superimpose the plurality of corrected first X-ray images.

Therefore, the image processing apparatus according to the present embodiment can perform the processing performed in the image processing method according to the first to sixth examples on a plurality of first X-ray images that have been corrected based on a second X-ray image as the processing target, for example. Further, after performing correction on a plurality of first X-ray images in the processing performed in the image processing method according to the first to sixth examples, for example, the image processing apparatus according to the present embodiment can also further correct based on the second X-ray image and superimpose the plurality of first corrected X-ray images.

(Image Processing Apparatus According to the Present Embodiment)

Next, an example of the configuration of an image processing apparatus according to the present embodiment that is capable of performing the processing performed in the above-described image processing method according to the present embodiment will be described.

Figure 19:
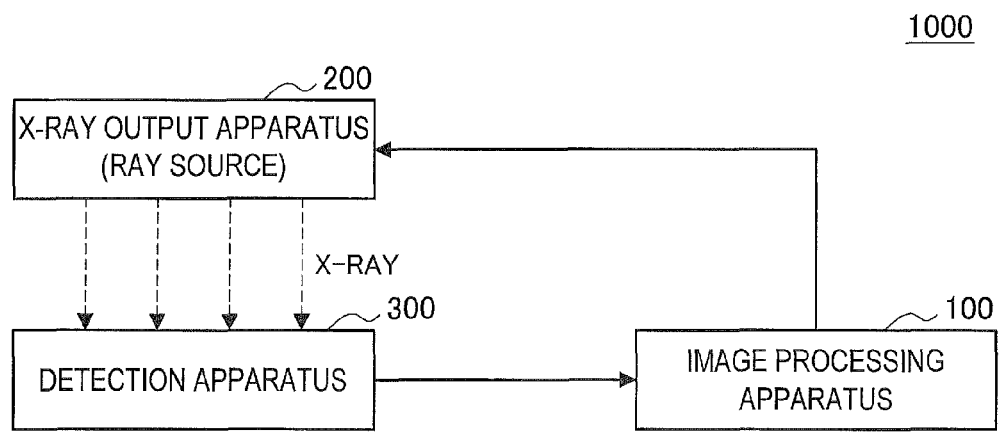
FIG. 19 is an explanatory diagram illustrating an example of an image processing system according to an embodiment of the present disclosure.

(I) Example of the Configuration of the Image Processing System According to the Present Embodiment Before describing an example of the configuration of the image processing apparatus according to the present embodiment, an example of the image processing system according to the present embodiment that has the image processing apparatus according to the present embodiment will be described. FIG. 19 is an explanatory diagram illustrating an example of an image processing system 1000 according to the present embodiment. The image processing system 1000 has, for example, an image processing apparatus 100, an X-ray output apparatus 200, and a detection apparatus 300.

The X-ray output apparatus 200 includes, for example, the ray source (not illustrated) according to the present embodiment, which includes a plurality of X-ray sources that output parallel beam X-rays, for outputting parallel beam X-rays from each X-ray source. Here, an example of the X-ray sources included in the ray source (not illustrated) according to the present embodiment is an X-ray tube, which is an electron tube for generating X-rays. Further, the X-ray output apparatus 200 includes a colimeter that forms parallel beam X-rays generated by thye X-ray sources. In addition, an example of the ray source according to the present embodiment included in the X-ray output apparatus 200 is a planar ray source in which a plurality of X-ray sources are arranged on a flat face.

It is noted that the configuration of the X-ray output apparatus 200 is not limited to that described above. For example, the X-ray output apparatus 200, which is configured from a MPU (micro-processing unit), various processing circuits and the like, may also include a control unit (not illustrated) for directly controlling the generation of X-rays by the ray source according to the present embodiment and the opening and closing of the collimator, a ROM (read-only memory, not illustrated), a RAM (not illustrated), a communication unit (not illustrated) and the like. The control unit (not illustrated) controls the generation of X-rays by the ray source according to the present embodiment and the opening and closing of the collimator based on control commands transmitted from the image processing apparatus 100.

Here, the ROM (not illustrated) included in the X-ray output apparatus 200 stores control data, such as programs and calculation parameters used by the control unit (not illustrated) included in the detection apparatus 300. The RAM included in the X-ray output apparatus 200 temporarily stores programs, for example, that are executed by the control unit (not illustrated) included in the X-ray output apparatus 200.

The communication unit (not illustrated) included in the X-ray output apparatus 200 is a communication device included in the X-ray output apparatus 200, which has the role of performing wireless/wired communication with an external device, such as the image processing apparatus 100, via a network (or directly). Here, examples of the communication unit (not illustrated) included in the X-ray output apparatus 200 include a communication antenna and an RF (radio frequency) circuit (wireless communication), an IEEE 802.15.1 port and a transmitting/receiving circuit (wireless communication), an IEEE 802.11b port and a transmitting/receiving circuit (wireless communication), or a LAN (local area network) terminal and a transmitting/receiving circuit (wired communication) and the like. Further examples of the communication unit (not illustrated) included in the X-ray output apparatus 200 include a configuration that supports an arbitrary standard capable of performing communication, such as a USB (universal serial bus) terminal and a transmitting/receiving circuit, and an arbitrary configuration capable of communicating with an external device via a network. Examples of the network according to an embodiment of the present disclosure include a wired network such as a LAN or a WAN (wide area network), a wireless network such as a wireless LAN (wireless local area network), and wireless WAN (wireless wide area network) via a base station, or the Internet using a communication protocol such as TCP/IP (transmission control protocol/internet protocol) and the like.

The detection apparatus 300, which includes a detection unit (not illustrated) that has a detector for detecting X-rays, for example, detects parallel beam X-rays and generates X-ray detection data.

It is noted that the configuration of the detection apparatus 300 is not limited to that described above. For example, the detection apparatus 300 is configured from a MPU, various processing circuits and the like. Further, the detection apparatus 300 may also include a processing unit (not illustrated) for converting X-ray detection data into projection data, a ROM (not illustrated), a RAM (not illustrated), a communication unit and the like.

Here, the ROM (not illustrated) included in the detection apparatus 300 stores control data, such as programs and calculation parameters used by the control unit (not illustrated) included in the detection apparatus 300. The RAM included in the detection apparatus 300 temporarily stores programs, for example, that are executed by the control unit (not illustrated) included in the detection apparatus 300.

The communication unit (not illustrated) included in the detection apparatus 300 is a communication device included in the detection apparatus 300, which has the role of performing wireless/wired communication with an external device, such as the image processing apparatus 100, via a network (or directly). Here, examples of the communication unit (not illustrated) included in the detection apparatus 300 include a communication antenna and an RF circuit (wireless communication), an IEEE 802.15.1 port and a transmitting/receiving circuit (wireless communication), an IEEE 802.11b port and a transmitting/receiving circuit (wireless communication), or a LAN terminal and a transmitting/receiving circuit (wired communication) and the like. Further examples of the communication unit (not illustrated) included in the detection apparatus 300 include a configuration that supports an arbitrary standard capable of performing communication, such as a USB terminal and a transmitting/receiving circuit, and an arbitrary configuration capable of communicating with an external device via a network.

The detection apparatus 300 transmits to the image processing apparatus 100, for example, the generated X-ray detection data and projection data in which X-ray detection data has been converted.

The image processing apparatus 100 performs the above-described processing performed in the image processing method according to the present embodiment.

Here, the image processing apparatus 100 processes, for example, X-ray detection data transmitted from the detection apparatus 300, and projection data transmitted from the detection apparatus 300 in which X-ray detection data has been converted. It is noted that the image processing apparatus 100 can process, for example, X-ray detection data stored in a storage unit (described below) or the like, and projection data stored in the storage unit (described below) in which X-ray detection data has been converted. Examples of X-ray detection data stored in the storage unit (described below) or the like include X-ray detection data corresponding to a detection result of X-rays output from the ray source according to the present embodiment, such as X-ray detection data generated by the detection apparatus 300. Further, examples of projection data stored in the above-described storage unit (described below) or the like in which X-ray detection data has been converted include projection data in which X-ray detection data corresponding to the detection result of X-rays output from the ray source according to the present embodiment has been converted, such as projection data converted by the detection apparatus 300.

The image processing system 1000 has, for example, the configuration illustrated in FIG. 19. In the image processing system 1000 illustrated in FIG. 19, an X-ray image corresponding to the target is obtained by the image processing apparatus 100 performing the above-described processing performed in the image processing method according to the present embodiment. Therefore, based on the configuration illustrated in FIG. 19, for example, an image processing system is realized that can achieve a higher quality X-ray image.

Further, in the image processing system 1000 illustrated in FIG. 19, the image processing apparatus 100 superimposes the plurality of X-ray images that are based on X-ray detection data representing each detection result obtained by detecting a plurality of times in a time-division manner at the detection apparatus 300 parallel beam X-rays output from the ray source according to the present embodiment by performing the processing performed in the above-described image processing method according to the present embodiment. Therefore, based on the configuration illustrated in FIG. 19, for example, an image processing system is realized capable of reducing the exposure of the target. Further, based on the configuration illustrated in FIG. 19, for example, processing can be speeded up by the image processing apparatus 100, and an image processing system can be realized that is capable of reducing the memory amount used in the processing by the image processing apparatus 100.

It is noted that the image processing system according to the present embodiment is not limited to the configuration illustrated in FIG. 19. For example, in the image processing system according to the present embodiment, the X-ray output apparatus 200 and the detection apparatus 300 may be an integrated apparatus, like a CT apparatus that utilizes X-rays or an apparatus having a tomosynthesis function in which X-rays are utilized. Further, if the X-ray output apparatus 200 and the detection apparatus 300 are an integrated apparatus, such an apparatus may include a gantry that has a rotary motor, for example.

(II) Example of the Configuration of the Image Processing Apparatus According to the Present Embodiment Next, an example of the configuration of the image processing apparatus according to the present embodiment will be described using the image processing apparatus 100 configuring the image processing system 1000 illustrated in FIG. 19 as an example.

Figure 20:
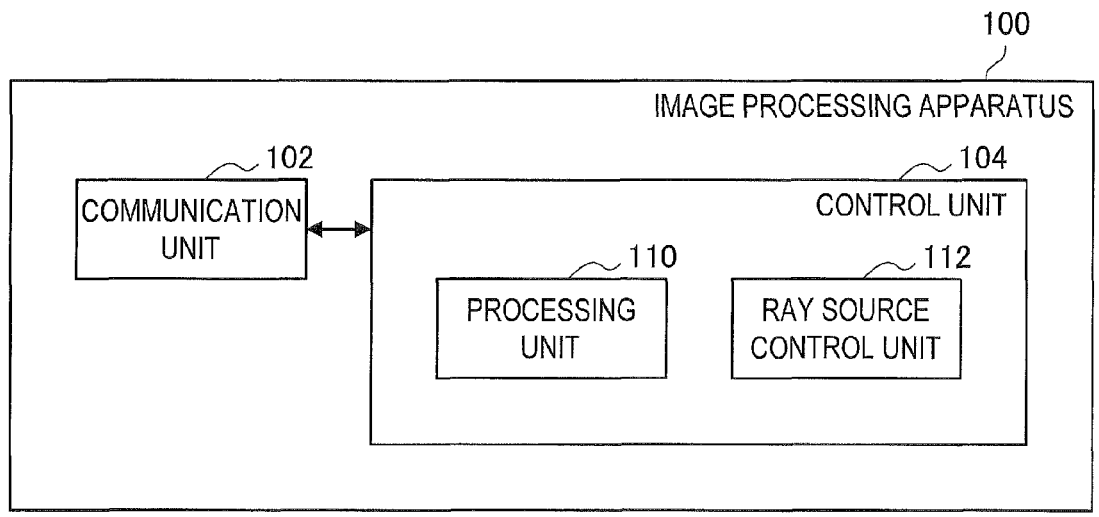
FIG. 20 is a block diagram illustrating an example of a configuration of an image processing apparatus according to an embodiment of the present disclosure.

FIG. 20 is a block diagram illustrating an example of a configuration of an image processing apparatus 100 according to an embodiment of the present disclosure. The image processing apparatus 100 includes, for example, a communication unit 102 and a control unit 104.

Further, the image processing apparatus 100 may also include, for example, a ROM (not illustrated), a RAM (not illustrated), a storage unit (not illustrated), a user-operable operation unit (not illustrated), a display unit (not illustrated) that displays various screens on a display screen and the like. The image processing apparatus 100 connects these constituent elements to each other with a bus that serves as a data transmission path.

Here, the ROM (not illustrated) stores control data, such as programs and calculation parameters used by the control unit 104. The RAM (not illustrated) temporarily stores programs and the like that are executed by the control unit 104.

The storage unit (not illustrated) is a storage device included in the image processing apparatus 100, which stores, for example, various data such as X-ray detection data, projection data in which X-ray detection data has been converted, data representing an X-ray image, and applications. Here, examples of the storage unit (not illustrated) include magnetic recording media such as a hard disk, non-volatile memory such as flash memory and the like. Further, the storage unit (not illustrated) may be detachable from the image processing apparatus 100.

Examples of the operation unit (not illustrated) include the below-described operation input device. Examples of the display unit (not illustrated) may include the below-described display device.

(Hardware Configuration Example of the Image Processing Apparatus 100)

FIG. 21 is an explanatory diagram illustrating an example of a hardware configuration of the image processing apparatus 100 according to an embodiment of the present disclosure. The image processing apparatus 100 includes, for example, a MPU 150, a ROM 152, a RAM 154, a recording medium 156, an input/output interface 158, an operation input device 160, a display device 162, and a communication interface 164. Further, the image processing apparatus 100 connects these constituent elements to each other with a bus 166 that serves as a data transmission path, for example.

The MPU 150 is configured from, for example, a MPU, various processing circuits and the like. The MPU 150 functions as the control unit 104 for controlling the whole image processing apparatus 100. Further, in the image processing apparatus 100, the MPU 150 plays the role of, for example, the below-described processing unit 110 and the ray source control unit 112.

The ROM 152 stores control data, such as programs and calculation parameters used by the MPU 150. The RAM 154 temporarily stores programs and the like, for example, that are executed by the MPU 150.

The recording medium 156 functions as a storage unit (not illustrated), which stores, for example, various data such as X-ray detection data, projection data in which X-ray detection data has been converted, data representing an X-ray image, and applications. Here, examples of the recording medium 156 include magnetic recording media such as a hard disk, non-volatile memory such as flash memory and the like. Further, the recording medium 156 may be detachable from the image processing apparatus 100.

The input/output interface 158, for example, connects the operation input device 160 and the display device 162. The operation input device 160 functions as an operation unit (not illustrated), and the display device 162 functions as a display unit (not illustrated). Here, examples of the input/output interface 158 include a USB terminal, a DVI (digital visual interface) terminal, a HDMI® (high-definition multimedia interface) terminal, various processing circuits and the like. Further, the operation input device 160 is, for example, included on the image processing apparatus 100, and is connected with the input/output interface 158 in the image processing apparatus 100. Examples of the operation input device 160 include a button, a direction key, a rotating-type selector such as a jog dial, or a combination of these. Further, the display device 162 is, for example, included on the image processing apparatus 100, and is connected with the input/output interface 158 in the image processing apparatus 100. Examples of the input/output interface 158 include a liquid crystal display (LCD), an organic EL display (organic electroluminescence display, also called an OLED (organic light emitting diode display)) and the like.

It is noted that the input/output interface 158 is obviously also connected to an external device, such as an operation input device (e.g., a keyboard, a mouse etc.) or a display device, as an external device of the image processing apparatus 100. Further, the display device 162 may also be a device that can perform a display and user operations.

The communication interface 164 is a communication unit included in the image processing apparatus 100, which functions as the communication unit 102 for performing wireless/wired communication with the X-ray output apparatus 200 or an external device, such as the detection apparatus 300 or a server, via a network (or directly). Here, examples of the communication interface 164 include a communication antenna and an RF circuit (wireless communication), an IEEE 802.15.1 port and a transmitting/receiving circuit (wireless communication), an IEEE 802.11b port and a transmitting/receiving circuit (wireless communication), or a LAN terminal and a transmitting/receiving circuit (wired communication) and the like.

Based on the configuration illustrated in FIG. 21, for example, the image processing apparatus 100 performs the processing performed in the image processing method according to the present embodiment. It is noted that the hardware configuration of the image processing apparatus 100 according to the present embodiment is not limited to the configuration illustrated in FIG. 21. If the image processing apparatus 100 performs processing as a standalone configuration, for example, when the image processing apparatus 100 includes the ray source according to the present embodiment included in the X-ray output apparatus 200, the detector included in the detection apparatus 300 and the like, the image processing apparatus 100 may be configured without the communication interface 164. In addition, the image processing apparatus 100 may also be configured without the operation input device 160 or the display device 162.

An example of the configuration of the image processing apparatus 100 will be described again with reference to FIG. 20. The communication unit 102 is a communication unit included in the image processing apparatus 100, which performs wireless/wired communication with the X-ray output apparatus 200 or an external device, such as the detection apparatus 300 or a server, via a network (or directly). Further, communication by the communication unit 102 is controlled by the control unit 104, for example.

Here, examples of the communication unit 102 include a communication antenna and an RF (radio frequency) circuit, a LAN terminal, a transmitting/receiving circuit and the like. However, the configuration of the communication unit 102 is not limited to these examples. For example, the communication unit 102 may have a configuration that supports an arbitrary standard that is capable of performing communication, such as a USB terminal and a transmitting/receiving circuit, or an arbitrary configuration that is capable of communicating with an external device via a network.

The control unit 104 is configured from a MPU, for example, which plays the role of controlling the whole image processing apparatus 100. Further, the control unit 104 which includes, for example, the processing unit 110 and the ray source control unit 112, plays the lead role in the processing performed in the image processing method according to the present embodiment.

The processing unit 110 performs the lead role in the above-described processing (composite processing) of (I), by superimposing a plurality of X-ray images that are based on X-ray detection data representing each detection result obtained a plurality of times in a time-division manner by detecting parallel beam X-rays output from the ray source according to the present embodiment. More specifically, the processing unit 110 performs the processing performed in any of the above-described first to seventh examples.

Here, in the case of performing the processing according to the above-described first to sixth examples, the plurality of X-ray images according to the present embodiment that are based on X-ray detection data representing each detection result obtained by detecting a plurality of times in a time-division manner, which are the target of processing by the processing unit 110, are X-ray images in which an area overlapping with another X-ray image is not present (first X-ray images). In this case, the processing unit 110 superimposs the plurality of X-ray images in which an overlapping area is not present (alternatively, the plurality of X-ray images in which an overlapping area is not present that have been corrected by the processing performed in the image processing method according to the above-described second to sixth examples).

Further, in the case of performing the processing according to the above-described seventh example, the plurality of X-ray images according to the present embodiment that are based on X-ray detection data representing each detection result obtained by detecting a plurality of times in a time-division manner, which are the target of processing by the processing unit 110, include a plurality of X-ray images in which an area overlapping with another X-ray image is not present (first X-ray images) and an X-ray image in which an area overlapping with each of a plurality of X-ray images in which an overlapping area is not present is present (second X-ray image). In this case, the processing unit 110 corrects each of the plurality of X-ray images in which an overlapping area is not present (alternatively, the plurality of X-ray images in which an overlapping area is not present that have been corrected by the processing performed in the image processing method according to the above-described second to sixth example) based on the X-ray image in which an overlapping area is present. Further, the processing unit 110 superimposes the plurality of corrected X-ray images in which an area overlapping with another X-ray image is not present.

The ray source control unit 112 performs the lead role in the above-described processing (ray source control processing) of (II), by controlling the acquisition of a plurality of X-ray images that are based on X-ray detection data representing each detection result obtained by detecting a plurality of times in a time-division manner, by controlling the ray source according to the present embodiment (an example of the ray source according to the present embodiment) included in the X-ray output apparatus 200, for example. More specifically, the ray source control unit 112 performs the processing performed in any of the above-described (A) to (C) based on the transmission of a control command to the X-ray output apparatus 200 by the communication unit 102, for example.

The control unit 104 includes the processing unit 110 and the ray source control unit 112, for example, which enables it to perform the lead role in the above-described processing (composite processing) of (I) and the above-described processing (ray source control processing) of (II) processing performed in the image processing method according to the present embodiment.

The image processing apparatus 100 performs the processing performed in the image processing method according to the present embodiment based on the configuration illustrated in FIG. 20, for example.

Therefore, the image processing apparatus 100 can improve the image quality of an X-ray image.

Further, the image processing apparatus 100 processes a plurality of X-ray images that are based on X-ray detection data representing each detection result obtained a plurality of times in a time-division manner by detecting parallel beam X-rays output from the ray source according to the present embodiment, for example. Therefore, the image processing apparatus main unit 100 can speed up the processing, and can reduce the memory amount that is used in processing.

It is noted that the configuration of the image processing apparatus according to the present embodiment is not limited to the configuration illustrated in FIG. 20.

(I) FIRST MODIFIED EXAMPLE

For example, the image processing apparatus according to the present embodiment can have a configuration that does not include the ray source control unit 112 illustrated in FIG. 20. Even without including the ray source control unit 112, the image processing apparatus according to the first modified example of the present embodiment can perform the above-described processing (composite processing) of (I) that is performed in the image processing method according to the present embodiment. Therefore, the image processing apparatus according to the first modified example of the present embodiment can enjoy the same advantageous effects as the main unit 100 illustrated in FIG. 20.

(II) SECOND MODIFIED EXAMPLE

Further, the image processing apparatus according to the present embodiment can also further include a detection unit (not illustrated) having the same function and configuration as the detection apparatus 300 illustrated in FIG. 19. The detection unit (not illustrated) generates X-ray detection data by detecting parallel beam X-rays. Further, for example, the detection unit (not illustrated) may also have a function for generating X-ray detection data by detecting parallel beam X-rays and converting the generated parallel X-ray data into projection data.

If the detection unit (not illustrated) does generate X-ray detection data by detecting parallel beam X-rays, the processing unit 110 processes the X-ray images that are based on the generated X-ray detection data with the detection unit (not illustrated). The processing unit 110 according to the second modified example of the present embodiment may also process X-ray detection data stored in a storage unit (described below) or projection data converted from X-ray detection data stored in a storage unit (described below).

Even with a configuration that further includes a detection unit (not illustrated), similar to the main unit 100 illustrated in FIG. 18, the image processing apparatus according to the second modified example of the present embodiment can perform the above-described processing (composite processing) of (I) and the above-described processing (ray source control processing) of (II) that are performed in the image processing method according to the present embodiment. Therefore, the image processing apparatus according to the second modified example of the present embodiment can enjoy the same advantageous effects as the main unit 100 illustrated in FIG. 18.

(III) THIRD MODIFIED EXAMPLE

The image processing apparatus according to the present embodiment can also further include the ray source (not illustrated) according to the present embodiment that has the same function and configuration as the ray source according to the present embodiment included in the X-ray output apparatus illustrated in FIG. 19. The ray source (not illustrated) according to the present embodiment that is included in the image processing apparatus according to the third modified example of the present embodiment is controlled by, for example, the ray source control unit 112.

Even with a configuration that further includes the ray source according to the present embodiment (not illustrated), similar to the main unit 100 illustrated in FIG. 20, the image processing apparatus according to the third modified example of the present embodiment can perform the above-described processing (composite processing) of (I) and the above-described processing (ray source control processing) of (II) that are performed in the image processing method according to the present embodiment. Therefore, the image processing apparatus according to the third modified example of the present embodiment can enjoy the same advantageous effects as the main unit 100 illustrated in FIG. 20.

(IV) OTHER MODIFIED EXAMPLES

The image processing apparatus according to the present embodiment can also be an arbitrary combinable configuration of, for example, the "combined configuration of the first modified example and the second modified example", the "combined configuration of the first modified example and the third modified example", the "combined configuration of the second modified example and the third modified example", the "combined configuration of the first modified example, the second modified example, and the third modified example" and the like.

Further, when performing processing as a standalone configuration, or when performing communication with an external apparatus such as the X-ray output apparatus 200 via an external communication apparatus having the same function as the communication unit 102, the image processing apparatus according to the present embodiment may also be configured without the communication unit 102.

Although an image processing apparatus was described above as an embodiment of the present disclosure, the present embodiment is not limited to this example. The present embodiment can also be used in various devices that are capable of processing an image, such as a computer like a PC (personal computer) and a server, a CT apparatus (an apparatus that uses 360° direction projection data), an apparatus having a tomosynthesis function (e.g., an apparatus that uses projection data in a restricted angle direction), such as less than 180°), a tablet type device, a communications device such as a mobile phone or a smartphone. Further, the present embodiment can also be applied in a processing IC (integrated circuit) that can be incorporated in such devices.

(Program According to the Present Embodiment)

The image quality of an X-ray image can also be improved by executing on a computer a program (e.g., a program capable of executing the processing performed in the image processing method according to the present embodiment, such as a program capable of executing the "processing (composite processing) of (I)" and the "processing (ray source control processing) of (II)") that makes the computer function as the image processing apparatus according to the present embodiment.

It should be understood by those skilled in the art that various modifications, combinations, sub-combinations and alterations may occur depending on design requirements and other factors insofar as they are within the scope of the appended claims or the equivalents thereof.

For example, although a program (computer program) that makes a computer function as the image processing apparatus according to the present embodiment was described above, the present embodiment can further provide a recording medium in which this program is stored.

The above-described configuration illustrates one example of the present embodiment, and naturally comes under the technical scope of an embodiment according to the present disclosure.

Additionally, the present technology may also be configured as below.

(1) An image processing apparatus including:
  a processing unit configured to superimpose a plurality of X-ray images that are based on X-ray detection data representing detection results obtained by detecting a plurality of times in a time-division manner parallel beam X-rays output from a ray source including a plurality of X-ray sources that output parallel beam X-rays.

(2) The image processing apparatus according to (1),
  wherein the processing unit is configured to
    correct an X-ray intensity of the plurality of X-ray images based on a plurality of calibration images that are based on the X-ray detection data representing each detection result in a state in which a target is not present, and
    superimpose the plurality of corrected X-ray images.

(3) The image processing apparatus according to (2),
  wherein the processing unit is further configured to correct the X-ray intensity of the plurality of X-ray images based on an offset image that is based on the X-ray detection data in a state in which a target is not present, and a state in which X-rays have not been output.

(4) The image processing apparatus according to any one of (1) to (3),
  wherein the processing unit is configured to
    correct, based on a detection result of positional deviation among the plurality of X-ray images, the positional deviation among the detected X-ray images, and
    superimpose the plurality of X-ray images in which the positional deviation has been corrected.

(5) The image processing apparatus according to (4),
  wherein the processing unit is configured to
    correct positional deviation of a plurality of calibration images that are based on the X-ray detection data representing each detection result in a state in which a target is not present, based on a detection result of the positional deviation among the X-ray images,
    correct an X-ray intensity of the plurality of X-ray images in which the positional deviation has been corrected based on the plurality of calibration images in which the positional deviation has been corrected, and
    superimpose the plurality of X-ray images in which the positional deviation has been corrected.

(6) The image processing apparatus according to any one of (1) to (5), further including:
  a ray source control unit configured to control acquisition of the plurality of X-ray images by controlling the ray source.

(7) The image processing apparatus according to (6),
  wherein the ray source control unit is configured to control selective output of X-rays from each of the plurality of X-ray sources included in the ray source.

(8) The image processing apparatus according to (6),
  wherein the ray source includes a plurality of collimators that selectively let X-rays pass through, the plurality of collimators corresponding to the respective X-ray sources, and
  wherein the ray source control unit is configured to control transmission of X-rays at each of the collimators.

(9) The image processing apparatus according to (6),
  wherein the ray source includes one or two or more collimators that let X-rays output from the X-ray sources pass through, and
  wherein the ray source control unit controls the X-rays that pass through the collimators by changing positions of the collimators.

(10) The image processing apparatus according to any one of (1) to (9), further including:
  a detection unit configured to detect the parallel beam X-rays output from the ray source,
  wherein the processing unit is configured to superimpose the plurality of X-ray images that are based on X-ray detection data representing detection results of the detection unit.

(11) The image processing apparatus according to any one of (1) to (11),
  wherein each of the plurality of X-ray images that are based on the X-ray detection data representing each detection result does not have an area overlapping with another X-ray image, and
  wherein the processing unit is configured to superimpose the plurality of X-ray images, each of plurality of X-ray images not having the area overlapping with the other X-ray image.

(12) The image processing apparatus according to any one of (1) to (10),
  wherein the plurality of X-ray images that are based on the X-ray detection data representing each detection result include a plurality of X-ray images each of which does not have an area overlapping with another X-ray image and an X-ray image which has the area overlapping with each of the plurality of X-ray images each of which does not have the overlapping area, and wherein the processing unit is configured to
correct each of the plurality of X-ray images each of which does not have the overlapping area based on the X-ray image which has the overlapping area, and
superimpose the plurality of corrected X-ray images each of which does not have the overlapping area.
(13) The image processing apparatus according to any one of (1) to (12), further including:
the ray source.
(14) An image processing method including:
superimposing a plurality of X-ray images that are based on X-ray detection data representing detection results obtained by detecting a plurality of times in a time-division manner parallel beam X-rays output from a ray source including a plurality of X-ray sources that output parallel beam X-rays.
(15) A program that causes a computer to execute:
superimposing a plurality of X-ray images that are based on X-ray detection data representing detection results obtained by detecting a plurality of times in a time-division manner parallel beam X-rays output from a ray source including a plurality of X-ray sources that output parallel beam X-rays.

What is claimed is:

1. An image processing apparatus comprising:
a processing unit configured to superimpose a plurality of X-ray images that are based on X-ray detection data representing detection results obtained by detecting a plurality of times in a time-division manner parallel beam X-rays output from a ray source including a plurality of X-ray sources that output parallel beam X-rays.

2. The image processing apparatus according to claim 1, wherein the processing unit is configured to
correct an X-ray intensity of the plurality of X-ray images based on a plurality of calibration images that are based on the X-ray detection data representing each detection result in a state in which a target is not present, and
superimpose the plurality of corrected X-ray images.

3. The image processing apparatus according to claim 2, wherein the processing unit is further configured to correct the X-ray intensity of the plurality of X-ray images based on an offset image that is based on the X-ray detection data in a state in which a target is not present, and a state in which X-rays have not been output.

4. The image processing apparatus according to claim 1, wherein the processing unit is configured to
correct, based on a detection result of positional deviation among the plurality of X-ray images, the positional deviation among the detected X-ray images, and
superimpose the plurality of X-ray images in which the positional deviation has been corrected.

5. The image processing apparatus according to claim 4, wherein the processing unit is configured to
correct positional deviation of a plurality of calibration images that are based on the X-ray detection data representing each detection result in a state in which a target is not present, based on a detection result of the positional deviation among the X-ray images,
correct an X-ray intensity of the plurality of X-ray images in which the positional deviation has been corrected based on the plurality of calibration images in which the positional deviation has been corrected, and
superimpose the plurality of X-ray images in which the positional deviation has been corrected.

6. The image processing apparatus according to claim 1, further comprising:
a ray source control unit configured to control acquisition of the plurality of X-ray images by controlling the ray source.

7. The image processing apparatus according to claim 6, wherein the ray source control unit is configured to control selective output of X-rays from each of the plurality of X-ray sources included in the ray source.

8. The image processing apparatus according to claim 6, wherein the ray source includes a plurality of collimators that selectively let X-rays pass through, the plurality of collimators corresponding to the respective X-ray sources, and
wherein the ray source control unit is configured to control transmission of X-rays at each of the collimators.

9. The image processing apparatus according to claim 6, wherein the ray source includes one or two or more collimators that let X-rays output from the X-ray sources pass through, and
wherein the ray source control unit controls the X-rays that pass through the collimators by changing positions of the collimators.

10. The image processing apparatus according to claim 1, further comprising:
a detection unit configured to detect the parallel beam X-rays output from the ray source,
wherein the processing unit is configured to superimpose the plurality of X-ray images that are based on X-ray detection data representing detection results of the detection unit.

11. The image processing apparatus according to claim 1, wherein each of the plurality of X-ray images that are based on the X-ray detection data representing each detection result does not have an area overlapping with another X-ray image, and
wherein the processing unit is configured to superimpose the plurality of X-ray images, each of plurality of X-ray images not having the area overlapping with the other X-ray image.

12. The image processing apparatus according to claim 1, wherein the plurality of X-ray images that are based on the X-ray detection data representing each detection result include a plurality of X-ray images each of which does not have an area overlapping with another X-ray image and an X-ray image which has the area overlapping with each of the plurality of X-ray images each of which does not have the overlapping area, and
wherein the processing unit is configured to
correct each of the plurality of X-ray images each of which does not have the overlapping area based on the X-ray image which has the overlapping area, and
superimpose the plurality of corrected X-ray images each of which does not have the overlapping area.

13. The image processing apparatus according to claim 1, further comprising:
the ray source.

14. An image processing method comprising:
superimposing a plurality of X-ray images that are based on X-ray detection data representing detection results obtained by detecting a plurality of times in a time-division manner parallel beam X-rays output from a ray source including a plurality of X-ray sources that output parallel beam X-rays.

15. A program that causes a computer to execute:
superimposing a plurality of X-ray images that are based on X-ray detection data representing detection results obtained by detecting a plurality of times in a time-division manner parallel beam X-rays output from a ray source including a plurality of X-ray sources that output parallel beam X-rays.

* * * * *